United States Patent [19]

Kitamura et al.

[11] Patent Number: 5,532,942

[45] Date of Patent: Jul. 2, 1996

[54] AUTOMATIC APPARATUS FOR INSPECTING POWDERY PRODUCT

[75] Inventors: Hajime Kitamura, Ichihara; Masaru Takeuchi; Hideo Yoshikoshi, both of Hazaki-machi; Mikio Kitai, Mito; Takashi Chino, Iruma; Yuji Nogami, Kawaguchi; Hajime Yashiro, Sagara-cho; Keisuke Kato, Kawasaki, all of Japan

[73] Assignee: Shin-Etsu Chemical Co., Ltd., Japan

Related U.S. Application Data

[63] Continuation-in-part of PCT/JP92/00865, filed Jul. 7, 1992.

[21] Appl. No.: 983,862

[22] Filed: Jul. 6, 1993

[30] Foreign Application Priority Data

| Jul. 8, 1991 | [JP] | Japan | 3-167101 |
| Aug. 29, 1991 | [JP] | Japan | 3-218253 |
| Aug. 29, 1991 | [JP] | Japan | 3-218254 |
| Jan. 6, 1993 | [JP] | Japan | 5-000797 |

[51] Int. Cl.$^6$ .......................... G01N 1/00; G01N 35/00
[52] U.S. Cl. ................ 364/555; 364/550; 73/863.31; 73/864.81
[58] Field of Search .................... 364/555, 550, 364/552, 468, 473, 479, 500; 73/149, 863, 863.01, 863.31, 864.81

[56] References Cited

U.S. PATENT DOCUMENTS

| 3,831,006 | 8/1974 | Chaffin, III et al. | 235/375 |
| 4,525,071 | 6/1985 | Horowitz et al. | 366/152 |
| 4,930,086 | 5/1990 | Fukasawa | 364/468 |
| 5,083,591 | 1/1992 | Edwards et al. | 141/9 |
| 5,125,091 | 6/1992 | Staas, Jr. et al. | 395/650 |
| 5,231,585 | 7/1993 | Kobayashi et al. | 364/468 |

FOREIGN PATENT DOCUMENTS

| 47-6348 | 4/1972 | Japan . |
| 49-68792 | 7/1974 | Japan . |
| 50-5096 | 1/1975 | Japan . |
| 52-80879 | 7/1977 | Japan . |
| 56-37059 | 9/1981 | Japan . |
| 59-112265 | 6/1984 | Japan . |
| 59-212769 | 12/1984 | Japan . |
| 61-30863 | 2/1986 | Japan . |
| 61-84567 | 6/1986 | Japan . |

*Primary Examiner*—Emanuel T. Voeltz
*Assistant Examiner*—Edward Pipala
*Attorney, Agent, or Firm*—Parkhurst, Wendel & Burr

[57] ABSTRACT

An apparatus for automatically inspecting powdery products is disclosed having a plurality of automatic inspection devices each device processing, in parallel, a subdivision of a supplied sample of a powdery product. Each device is controlled by a corresponding terminal computer. To one terminal computer there are connected a device for reading sample information attached to the supplied powdery sample and a device for recording, on the sample subdivisions, information concerning conditions for inspection established by the terminal computer on the basis of the sample information read by the first reading device. To each of the other terminal computers there is connected a corresponding device for reading the information concerning conditions for inspection recorded on the subdivision of the sample. Each terminal computer controls the operation of the automatic inspection devices on the basis of the information concerning conditions for inspection read by each corresponding reading device.

10 Claims, 15 Drawing Sheets

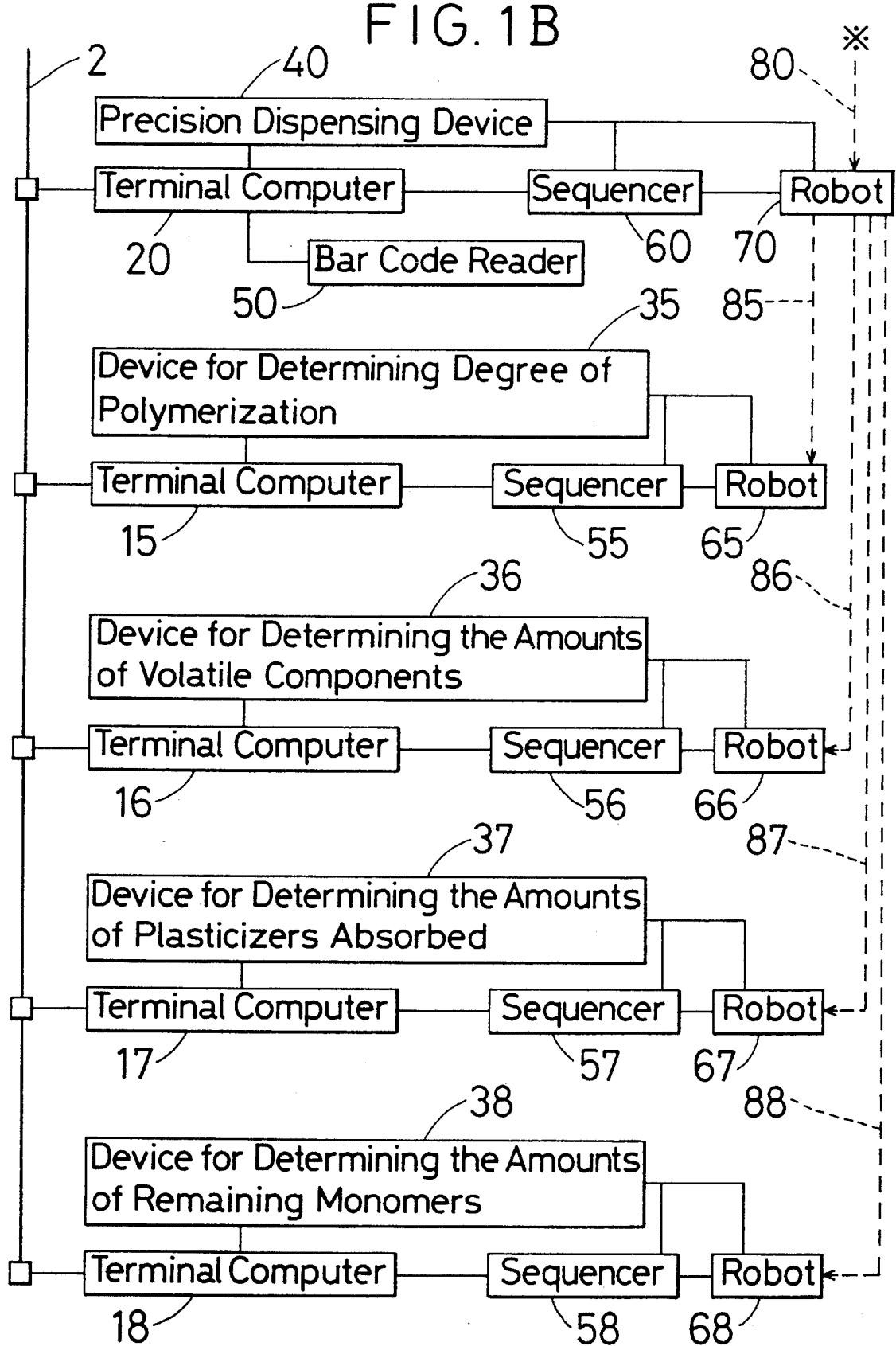

5,532,942

AUTOMATIC APPARATUS FOR INSPECTING POWDERY PRODUCT

This is a continuation-in-part of PCT/JP92/00865, filed Jul. 7, 1992.

BACKGROUND OF THE INVENTION

The present invention relates to an apparatus for automatically inspecting required characteristics of powdery products, for instance, powder of resins such as vinyl chloride resins, ABS resins and MBS resins and other powdery products such as powdery foods, for the purpose of quality control thereof.

When preparing, for instance, vinyl chloride resin powder and forwarding the products from a manufacturing plant, the quality control of the product is carried out, upon manufacture of the products, by inspecting samples thereof for predetermined properties, recording the results in a quality control table, sending back the table to the manufacturing plant to feedback the results into the manufacturing conditions of the products and, upon forwarding the products, a quality control table is commonly attached to the product in order to guarantee the quality thereof for user's convenience. The name of product, the kind thereof, the name of manufacturing plant, the manufacturing date and the number of manufacturing lot are recorded in the former quality control table and, on the other hand, the name of product, the kind thereof, the number of manufacturing lot and optionally the destination or the consignee are recorded in the latter quality control table.

For this reason, there is a diversity of items for quality inspection. For instance, the items for quality control of vinyl chloride resin powder include average degree of polymerization, bulk density, contents of volatile components, particle size distribution, amounts of foreign substances, amounts of remaining monomers, amounts of plasticizers absorbed and optional other items. An inspector appropriately selects items required for each sample (product) among the foregoing items required for quality control in accordance with a table including the foregoing items as well as other conditions such as the applications of the products and the destination or the consignee, collects necessary amounts of the samples and analyzes them using separate apparatuses required for the determination of these selected items. The results of such analysis are compared with the quality standards and judged. The results thus obtained are stored after recording in a report in the form of a quality control table or recording in a ledger.

In the conventional quality control system discussed above, however, items to be inspected often differ from sample to sample, it takes a long time since an inspector selects items to be inspected, collects and distributes samples to inspect them for the selected items and the inspector would sometimes make a wrong selection of items to be inspected. Moreover, results obtained through such inspection sometimes vary depending on inspectors. When the powdery product to be inspected is, for instance, a resin such as a vinyl chloride resin, an ABS resin or an MBS resin, the powdery product is liable to be charged in itself and accordingly, resin particles repulse each other due to electrostatic charges present on these particles. This makes the determination of the bulk density and the amounts of foreign substances included therein very difficult.

SUMMARY OF THE INVENTION

The present invention has been completed to solve these problems and to economize the apparatus for automatically inspecting powdery products. Accordingly, it is an object of the present invention to provide an apparatus for automatically inspecting powdery products which can provide reproducible accurate results.

According to the present invention, the foregoing object can effectively be accomplished by providing an apparatus for automatically inspecting powdery products comprising a plurality of automatic inspection devices each of which processes, in parallel, a subdivision obtained by subdividing a powdery sample supplied to the apparatus; a plurality of terminal computers; a device for reading sample information attached to the sample supplied and a device for recording, on each subdivision, information concerning conditions for inspection established by a first terminal computer among a plurality of the terminal computers on the basis of the read sample information, the reading device and the recording device being connected to the first terminal computer; a device for reading the information concerning the conditions for inspection attached to each subdivision, which is connected to a second terminal computer among a plurality of the terminal computers, which is connected to each corresponding automatic inspection device; whereby the terminal computer controls the operation of the corresponding automatic inspection device on the basis of the read information concerning the conditions for inspection.

The apparatus for automatically inspecting powdery products permits collective central processing of data (results) obtained through each inspection, permits storage, display and recording thereof in accordance with the usual manner and permits the comparison of the results with the quality standards for the judgment of the quality of the powdery products inspected. In other words, an inspector must not select items to be inspected for each sample and must be divide the sample into subdivisions. Further the results are automatically compared with the quality standards. Therefore, the judgment of the quality of the powdery products can rapidly and accurately be carried out.

When the automatic inspection apparatus comprises a device for determining bulk density and a bulk density-determining apparatus equipped with a static eliminator, the apparatus makes it possible to evaluate the charging properties of a resin powdery product such as a vinyl chloride resin, an ABS resin and an MBS resin which is liable to be charged in itself on the basis of the results of bulk density determination of the powder in electrostatically charged and destaticized states and this permits the understanding of errors encountered in volumetric measurement upon, for instance, manufacture of a powdery product.

BRIEF DESCRIPTION OF THE DRAWINGS

FIG. 1B is a block diagram illustrating an embodiment of the apparatus for automatically inspecting powdery products according to the present invention, which is continued from FIG. 1A;

DETAILED EXPLANATION OF THE INVENTION

Figure 1A:
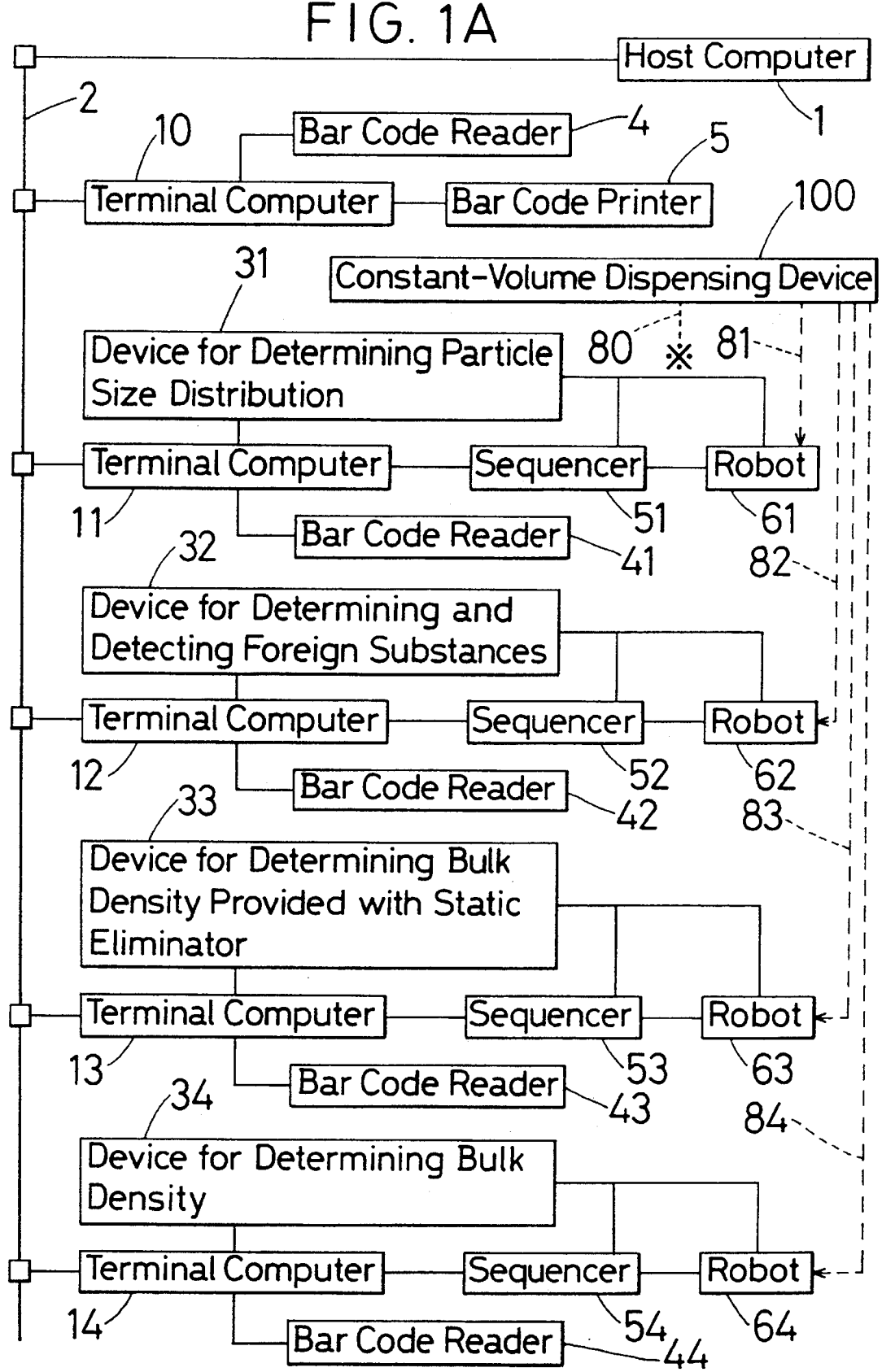
FIG. 1A is a block diagram illustrating an embodiment of the apparatus for automatically inspecting powdery products according to the present invention.

As specifically shown in FIGS. 1A and 1B which correspond to embodiments of the present invention, the apparatus for automatically inspecting powdery products according to the present invention comprises a plurality of automatic inspection devices 31, 32, 33, 34, 35, 36, 37, 38, and 40 which process, in parallel, subdivisions of a supplied powdery sample and the operations thereof are controlled by terminal computers 11/51; 12/52; 13/53; 14/54; 15/55; 16/56; 17/57; 18/58; and 20/60, respectively. A terminal computer 10 is connected to a device 4 for reading sample information attached to the supplied powdery sample and a device 5 for recording, on the subdivisions of the sample, information concerning the conditions for inspection established by the terminal computer 10 on the basis of the sample information read by the reading device 4. The terminal computers 11, 12, 13, 14 and 20 each is connected to each corresponding device 41, 42, 43, 44 or 45 for reading the information concerning the conditions for inspection recorded on each subdivision of the sample. The terminal computers 11/51, 12/52, 13/53, 14/54 and 20/60 each controls each corresponding automatic inspection device 31, 32, 33, 34 or 40 on the basis of the information concerning the conditions for inspection read by the corresponding reading device 41, 42, 43, 44 or 50.

Figure 2:
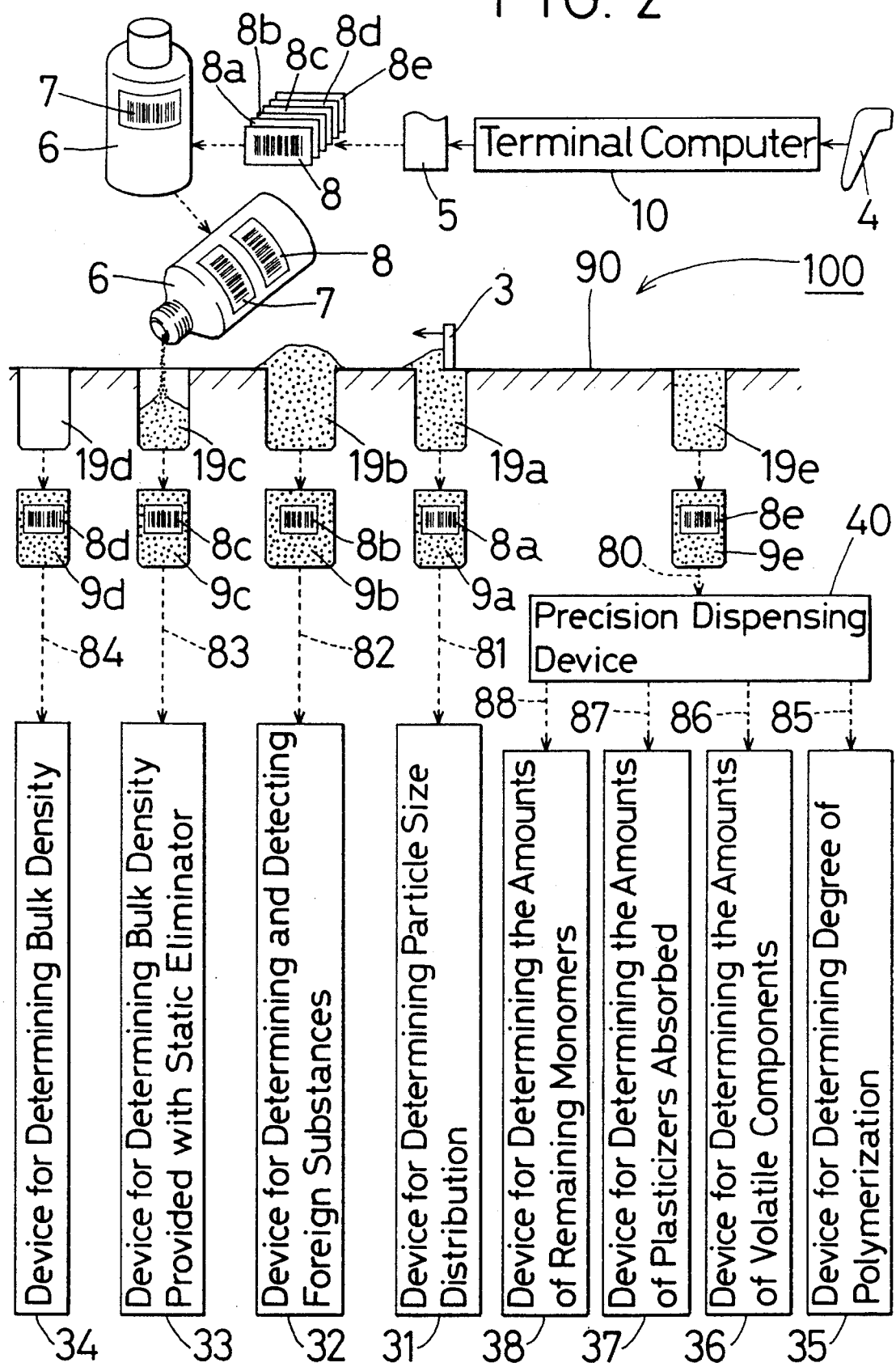
FIG. 2 is a diagram for explaining the order of operations of the apparatus for automatically inspecting powdery products according to the present invention.

As shown in FIG. 2, sample information 7 attached to the supplied powdery sample 6 and the information 8a to 8e concerning the conditions for inspection recorded on subdivisions 9a to 9e of the sample to be inspected are specifically bar code information. Thus, the device 4 for reading sample information 7 is a bar code reader, the device 5 for recording the information 8a to 8e concerning the conditions for inspection is a bar code printer and the device 41, 42, 43, 44 or 50 for reading the information concerning the conditions for inspection is a bar code reader.

It is preferred that the terminal computers 10 to 18 and 20 be connected to a host computer 1 so that the results obtained through the inspection by each automatic inspection device 31 to 38 or 40 be transferred to the host computer 1 together with the sample information and the information concerning the conditions for inspection, as seen from FIGS. 1A and 1B. The host computer 1 is preferably provided with a function for comparing the transferred inspection results with the inspection standards established on the basis of the sample information and the information concerning the conditions for inspection to thus judge the quality of the powdery product inspected.

As a plurality of automatic inspection devices fitted to the apparatus for automatically inspecting powdery products according to the present invention, there may be mentioned, for instance, a device for determining the amount of remaining monomers, a device for determining degree of polymerization, a device for determining the amounts of volatile components, a device for determining the amounts of plasticizers absorbed, a device for determining the particle size distribution, a device for detecting foreign substances and determining the amounts thereof, a device for determining bulk density and a device for determining bulk density provided with a static eliminator.

In addition, examples of samples to be inspected by the apparatus for automatically inspecting powdery products according to the present invention include vinyl chloride resin powder.

BEST MODE FOR CARRYING OUT THE INVENTION

Embodiments of the present invention will hereinafter be explained in more detail with reference to the accompanying drawings, but the present invention is by no means limited to these specific embodiments.

FIGS. 1A and 1B are block diagrams illustrating embodiments of the apparatus for automatically inspecting powdery products according to the present invention, in which FIG. 1B is continued from FIG. 1A.

The apparatus for automatically inspecting powdery products according to this embodiment is used for inspecting the quality of vinyl chloride resin powder as a powdery product. Items to be inspected include, for instance, the particle size distribution of the powder, the contents of foreign substances included in the powder, the bulk density of the powder observed when electrostatic charges thereof are destaticized, the bulk density thereof observed when electrostatic charges thereof are not destaticized, the average degree of polymerization, the amounts of volatile components included in the powder, the amounts of plasticizers absorbed and the amounts of monomers remaining in the powder.

As a whole, the apparatus comprises a host computer 1 and terminal computers 10 to 18 and 20 which are communicated to the host computer 1 through a local area network (LAN) 2, these computers serving as the control systems of the apparatus. The host computer 1, as a whole, controls the communication system comprising LAN 2 and allows the data communication between the host computer 1 and each terminal computer 10 to 18 or 20 and the data communication between the terminal computers 10 to 18 and 20. In addition, the host computer 1 serves to manage the number of powdery sample to be inspected, to intensively manage the data determined by each measuring device, as will be detailed below, through LAN 2 and to judge the quality of the powdery product by comparing the results of the inspection with the quality standards. Moreover, the host computer 1 serves to collectively report the data and the results of the judgment of the data.

Moreover, the host computer 1 comprises, as shown in the block diagram (FIG. 3), a central processing unit (CPU) 21 communicated to LAN 2 and memories 22 and 23. In the memory 22, there are stored the sample information, the quality standards and a program for judging the quality of the product. These sample information and the quality standards are previously inputted to the host computer 1 through an input unit 24 connected to CPU 21. The memory 23 is provided for storing the data of conditions for inspection, the results obtained through the inspection and the results of the quality judgment. CPU 21 is communicated to a printer 25 for recording various kinds of data and the results of the quality judgment and for preparing a report and a display device 26 for displaying these data, results and report.

As shown in FIGS. 1A and 1B, a bar code reader 4 and a bar code printer 5 are connected to the terminal computer 10 so as to read bar code labels and to record data in the bar code labels.

A device 31 for determining particle size distribution, a sequencer 51, a robot 61 and a bar code reader 41 are connected to the terminal computer 11. A conveyor 81 which extends from a constant volume-dispensing device 100 is positioned in the proximity of the bar code reader 41.

A device 32 for detecting foreign substances and determining the amounts thereof, a sequencer 52, a robot 62, and a bar code reader 42 are connected to the terminal computer 12. A conveyor 82 which extends from the constant volume-dispensing device 100 is positioned in the proximity of the bar code reader 42.

A device 33 for determining bulk density which is provided with a static eliminator, a sequencer 53, a robot 63 and a bar code reader 43 are connected to the terminal computer 13. A conveyor 83 which extends from the constant volume-dispensing device 100 is positioned in the proximity of the bar code reader 43.

A device 34 for determining bulk density, a sequencer 54, a robot 64 and a bar code reader 44 are connected to the terminal computer 14. A conveyor 84 which extends from the constant volume-dispensing device 100 is positioned in the proximity of the bar code reader 44.

A device 40 for precisely dispensing sample, a sequencer 60, a robot 70 and a bar code reader 50 are connected to the terminal computer 20. A conveyor 80 which extends from the constant volume-dispensing device 100 is positioned in the proximity of the bar code reader 50. Further conveyors 85, 86, 87 and 88 are positioned in the proximity of the robot 70.

A device 35 for determining degree of polymerization, a sequencer 55 and a robot 65 are connected to the terminal computer 15. The conveyor 85 which extends from the robot 70 of the device 40 for precisely dispensing sample is positioned in a region within which the robot 65 can move about.

A device 36 for determining the contents of volatile components, a sequencer 56 and a robot 66 are connected to the terminal computer 16. The conveyor 86 which extends from the robot 70 of the device 40 for precisely dispensing sample is positioned in a region within which the robot 66 can move about.

A device 37 for determining the amounts of plasticizers absorbed, a sequencer 57 and a robot 67 are connected to the terminal computer 17. The conveyor 87 which extends from the robot 70 of the device 40 for precisely dispensing sample is positioned in a region within which the robot 67 can move about.

A device 38 for determining the amounts of monomers remaining in the powdery product, a sequencer 58 and a robot 68 are connected to the terminal computer 18. The conveyor 88 which extends from the robot 70 of the device 40 for precisely dispensing sample is positioned in a region within which the robot 68 can move about.

The order of operations of the foregoing elements will be summarized below with reference to FIG. 2

A small amount of vinyl chloride resin powder is collected from that manufactured in a factory as a sample to be subjected to quality inspection. As shown in FIG. 2, the collected powdery sample is added to a sample bottle 6 and transported to the place at which an apparatus for automatically inspecting the powdery product is installed. To the sample bottle 6, there is pasted a bar code label 7 in which product data are recorded in the manufacturing plant, the data including, for instance, the name of the product, the kind thereof, the manufacturing line, the manufacturing date and the manufacturing lot number of the product.

When the sample is transported to the apparatus for automatically inspecting the powdery product, the bar code reader 4 reads the product data recorded in the bar code label 7 and the terminal computer 10 establishes the data of conditions for inspection including the inspection number, essential items for inspection and the conditions for inspection on the basis of the product data read by the bar code reader 4. For instance, terms for inspection and quality standards often differ from sample to sample depending on the kinds of the samples even if the names of powdery samples are the same. In this respect, deletion or correction of essential inspection items and conditions for inspection, arbitrary addition of inspection items and establishment of particular conditions for inspection can be inputted thereto through a keyboard. The data of conditions for inspection are inputted, together with the product data, to the host computer 1 through the terminal computer 10 and LAN 2. The product data are set in correspondence to the data of conditions for inspection in the host computer 1 and then these data are stored in the memory 23.

The terminal computer 10 converts the data of conditions for inspection into bar code data which are recorded in another bar code label 8 by the action of the bar code printer 5. Thus, the bar code label 8 representing the data of conditions for inspection are pasted on the sample bottle 6 in addition to the bar code label 7 representing the product data. Moreover, the bar code printer 5 prints out bar code labels 8a to 8e each of which carries the same data of conditions for inspection recorded in the bar code label 8. The bar codes recorded in these bar code labels 8, 8a to 8e, include the inspection number and specified inspection items selected from determination of particle size distribution, detection of foreign substances and determination of the amounts thereof, determination of bulk density, determination of bulk density after the electric charges are destaticized, determination of degree of polymerization, determination of the amounts of volatile components, determination of the amounts of plasticizers absorbed and determination of the contents of remaining monomers.

An embodiment in which all of the determination of the foregoing inspection items are carried out will be explained below.

The sample in a sample bottle 6 is subdivided into constant-volume sample berries 19a to 19e by a device 100 for dispensing a sample into constant-volume subdivisions. In the device 100, the constant-volume sample bottles 19a to 19e fitted into a table 90 are heaped with the sample included in the sample bottle 6 and the surface of the sample is leveled by a leveling bar 3 to dispense a constant volume of the sample. These constant-volume samples (subdivisions) dispensed in the constant-volume sample bottles 19a to 19e are poured into the corresponding sample bottles 9a to 9e for subdivision, respectively. The bar code labels 8a to 8e on which the data of conditions for inspection are printed are pasted on these sample bottles 9a to 9e for subdivision.

A dispensed subdivision of the sample in the sample bottle 9a is used for the determination of particle size distribution. A dispensed subdivision of the sample in the sample bottle 9b is used for the detection of foreign substances and determination of the amounts thereof. A dispensed subdivision of the sample in the sample bottle 9c is used for the determination of bulk density observed when electrostatic charges of the sample are destaticized. A dispensed subdivision of the sample in the sample bottle 9d is used for the determination of bulk density observed when electrostatic charges of the sample are not destaticized. A dispensed subdivision of the sample in the sample bottle 9e is used for further precise dispensing. The determination of the degree of polymerization, the contents of volatile components, the amounts of plasticizers absorbed and the contents of remaining monomers require the use of precisely weighed samples and thus the samples precisely dispensed from the sample included in the sample bottle 9e are used in these measurements. The sample bottle 9a for subdivision which contains the dispensed sample of a constant volume and on which the bar code label 8a is pasted is put on a conveyor 81 and transferred to a device 31 for determining particle size distribution. The sample bottle 9b for subdivision which contains the dispensed sample of a constant volume and on which the bar code label 8b is pasted is put on a conveyor 82 and transferred to a device 32 for detecting foreign substances and determining the amounts thereof. The sample bottle 9c for subdivision which contains the dispensed sample of a constant volume and on which the bar code label 8c is pasted is put on a conveyor 83 and transferred to a device 33 for determining bulk density provided with a static eliminator. The sample bottle 9d for subdivision which contains the dispensed sample of a constant volume and on which the bar code label 8d is pasted is put on a conveyor 84 and transferred to a device 34 for determining bulk density. The sample bottle 9e for subdivision which contains the dispensed sample of a constant volume and on which the bar code label 8e is pasted is put on a conveyor 80 and transferred to the device 40 for precisely dispensing sample.

The subdivisions prepared above are, subjected to determinations or precise dispensing as follows in accordance with the block diagrams shown in FIGS. 1A and 1B.

[Determination of Particle Size Distribution]

Figure 4:
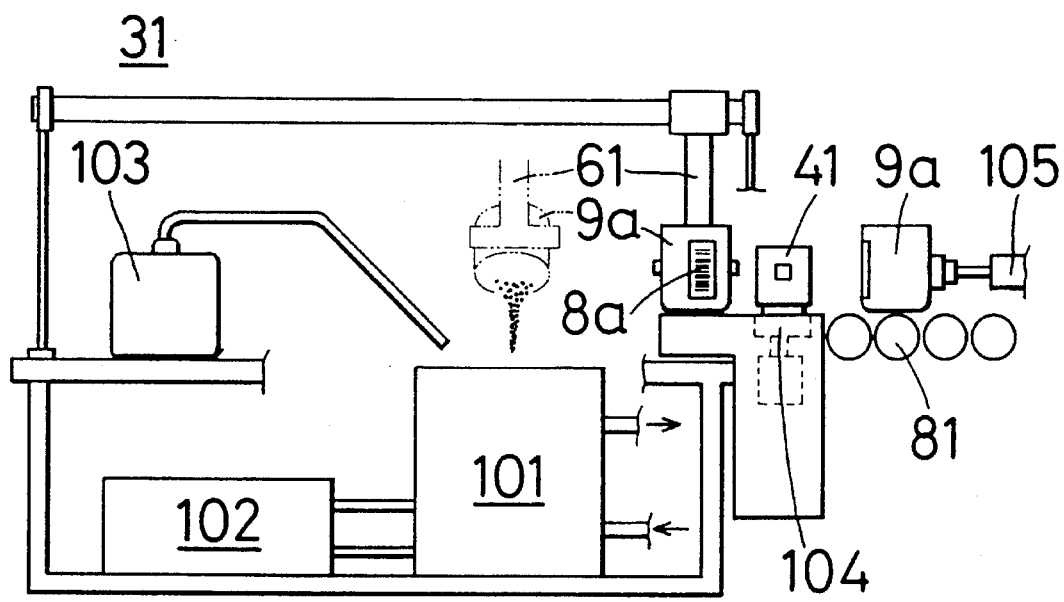
FIG. 4 is an elevational view of a device for determining particle size distribution.

As shown in the elevational view (FIG. 4), there are fitted, to the device 31 for determining particle size distribution, a sample circulator 101 for preparing a suspension of the powder sample and circulating the same and a particle size distribution-determining instrument 102 through piping. The particle size distribution-determining instrument 102 may be, for instance, a particle size distribution-determining instrument, Microtruck MK-II, available from Nikkiso Co., Ltd. The sample circulator 101 may be, for instance, an automatic large-volume sample circulator, LVR-AS, likewise available from Nikkiso Co., Ltd. A robot 61 which holds and transports the sample bottle 9a for subdivision and can rotate is fitted to the upper portion of the device. Moreover, there are also arranged within the device 31 a device 103 for supplying a dispersant (a surfactant) to the sample contained in the sample bottle 9a and an ultrasonic homogenizer (not shown). The sample circulator 101 is provided with a pipe for supplying purified water thereto and a drain for discarding the suspension after the determination.

The terminal computer 11 controls the determination of particle size distribution. The subdivision of the sample in the sample bottle 9a conveyed by the conveyor 81 is pushed by an air cylinder 105 and put on a turn table 104. The data of conditions for inspection recorded in the bar code label 8a pasted on the sample bottle 9a for subdivision are read by the bar code reader 41 and inputted to the terminal computer 11 which directs the apparatus for determining particle size distribution to perform the determination of the particle size distribution of the sample during rotating the turn table 104. The dispersant-supplying device 103 supplies a dispersant to the sample bottle 9a transferred by the robot 61 which operates through the action and control of the sequencer 51, further water is added thereto and the sample is dispersed by the ultrasonic homogenizer (not shown). After completion of the dispersion, the dispersed sample in the sample bottle 9a is poured into the sample circulator 101 by the action of the robot 61. In the sample circulator 101, a constant amount of water is added to the sample to form a suspension which is prepared and uniformly dispersed by circulation. The sample circulator 101 circulates the resulting suspension through the particle size distribution-determining device 102 in which the particle size distribution is determined. The determination of particle size distribution is, in principle, performed by irradiating particles present in the suspension with a laser beam to determine the intensity of diffracted light and the scattering angle observed when the laser beam is diffracted and scattered by the particles. The particle size is then calculated from the intensity of the diffracted light and the scattering angle thus determined. The smaller the particle size, the lower the intensity of the diffracted light per unit area and the greater the scattering angle. The particle size distribution of the powdery product is calculated on the basis of the particle sizes thus obtained. The particle size distribution thus calculated is inputted to the terminal computer 11 as a result of inspection and transferred, through LAN 2, to the host computer 1 together with the data of conditions for inspection previously inputted to the computer 11.

[Detection of Foreign Substances and Determination of the Amounts Thereof]

Figure 5:
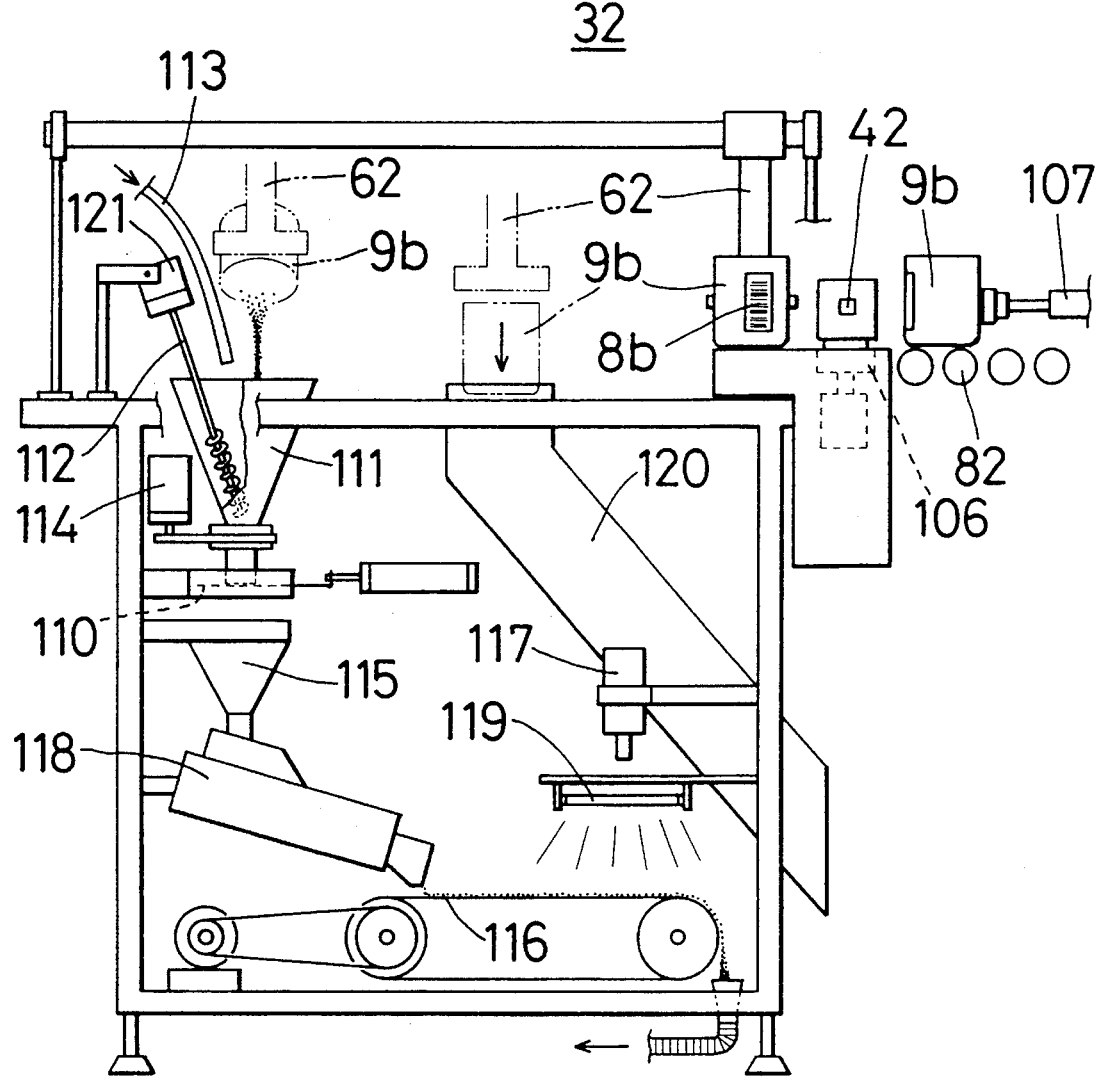
FIG. 5 is an elevational view of a device for detecting foreign substances and determining the amounts thereof.

As shown in the elevational view shown in FIG. 5, a device 32 for detecting foreign substances in the powdery products and determining the amounts thereof comprises, a video camera 117 which takes a photograph of a powdery sample which is dropped from a static eliminator and transferred, through a hopper 115, to a conveyor 116 on which it is spread and arranged in a uniform thickness. The image signal taken by the video camera 117 is digitized by an image signal processing and analysis circuit. As such a video camera means, there may be used, for instance, an industrial automatic visual inspecting device FF4000 available from Hajime Sangyo Co., Ltd. The static eliminator comprises a rotatable funnel 111 connected to a motor 114 in which a screw type stirring machine 112 connected to a motor 121 is inserted and a tube 113 communicated to a source of a destaticizing solution is introduced. The funnel 111 is provided with an electro-magnetic shutter 110. The device is equipped with a robot 62 which holds and transports the sample bottle 9b for subdivision and can rotate.

As shown in FIG. 1A, the foregoing device 32 for detecting foreign substances in the powdery products and determining the amounts thereof is connected to a sequencer 52, and the sequencer 52 is connected to a terminal computer 12. Further, a bar code reader 42 is connected to the terminal computer 12 and the terminal computer 12 is connected to the host computer 1 through local area network (LAN).

Figure 6:
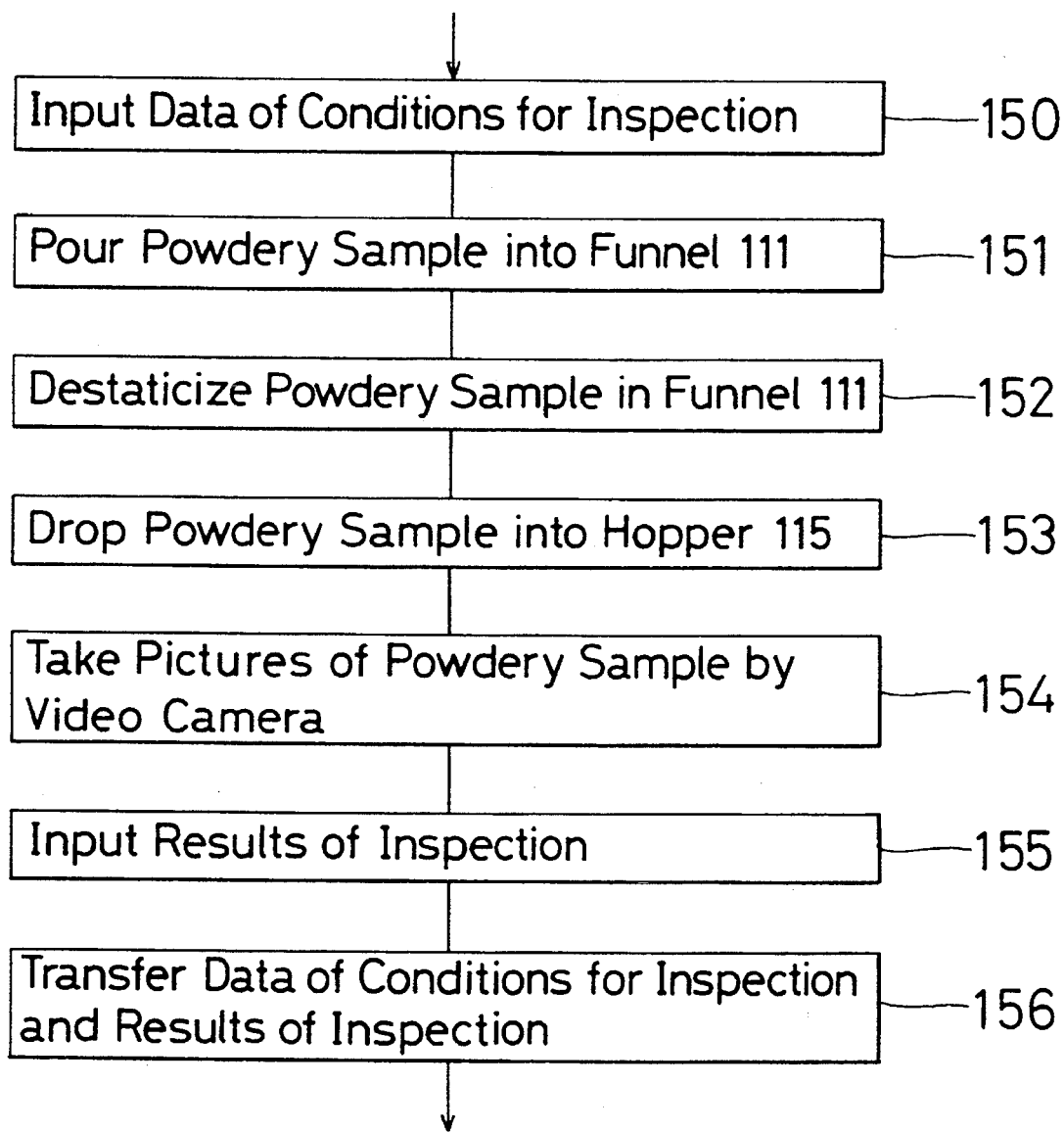
FIG. 6 is a flow chart showing the processing for detecting foreign substances and determining the amounts thereof.

The device for detecting foreign substance in powdery products and determining the amounts thereof operates as follows. The control, as a whole, is controlled in accordance with a program of the terminal computer 12 and the individual operations of the device are controlled in accordance with a control program of the sequencer 52. The order of operations will be summarized below in accordance with a program chart of the terminal computer 12 and the sequencer 52 shown in FIG. 6.

The subdivision of the sample in the sample bottle 9b conveyed by the conveyor 82 is pushed by an air cylinder 107 and put on a turn table 106. The data of conditions for inspection recorded in the bar code label 8b pasted on the sample bottle 9b for subdivision are read by the bar code reader 42 and, as shown in step 150, inputted to the terminal computer 12 which directs the apparatus for determining particle size distribution to perform the detection of foreign substances of the sample and determination of the amounts thereof during rotating the turn table 106, then the action and control is shifted from the terminal computer 12 to the sequencer 52.

The powdery sample contained in the sample bottle 9b is poured into the funnel 111 by the robot 62 which operates through the action and control of the sequencer 52 as shown in step 151. According to the instruction of the sequencer 52, the destaticizing solution (a solution of a cationic surfactant) is fed into the funnel 111 through the tube 113, then the funnel 111 is rotated by the rotation of the motor 114 and the screw type stirring machine 112 is rotated by the rotation of the motor 121, and accordingly the powdery sample in the funnel 111 is destaticized as shown in step 152. On the other hand, the vacant sample bottle 9b is transferred by the robot 62 towards waste chute 120. As shown in step 153, the destaticized powdery sample in the funnel 111 is dropped into the hopper 115 by opening the electromagnetic shutter 110 and uniformly spread on the conveyor 116 through the hopper 115 and a path 118 for leveling. The video camera 117 takes a photograph of the spread powdery sample under the irradiation with lights from a xenon lamp 119 as shown in step 154.

The image signal of the powdery sample thus obtained is subjected to image analysis for digitizing the amount of the foreign substances. As shown in step 155, the digitized information is inputted to the terminal computer 12 as the results of inspection and transferred, through LAN 2, to the host computer 1 together with the data of conditions for inspection previously inputted to the computer 12 as shown in step 156.

[Determination of Bulk Density Observed When Sample is Destaticized]

Figure 7:
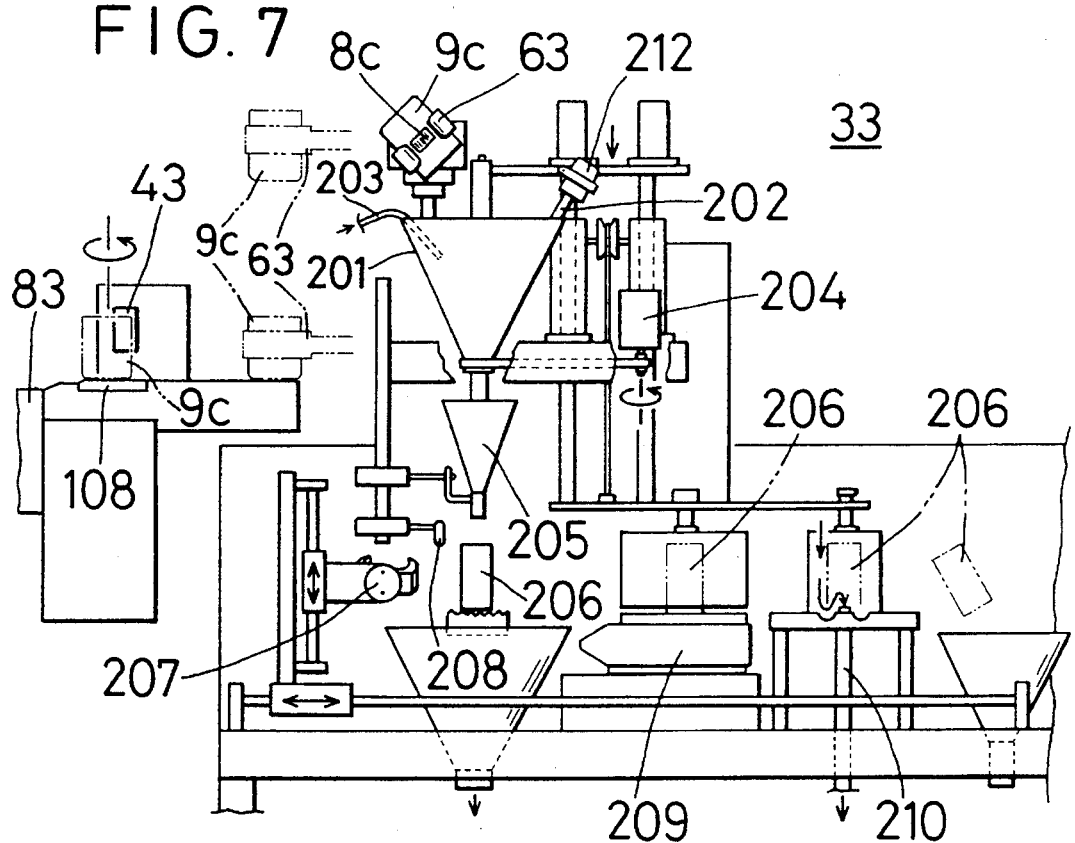
FIG. 7 is an elevational view of a bulk density-determining device equipped with a static eliminator.

As shown in the elevational view shown in FIG. 7, a device 33 for determining bulk density which is provided with a static eliminator comprises a sample-transporting robot 63 which holds and transports a sample bottle 9c containing a powdery sample and discharges the sample by turning the sample bottle 9c upside down. The device 33 comprises a rotatable funnel 201 which is connected to a motor 204 and receives the powdery sample and a screw stirring machine 202 which is connected to a motor 212 and a tube 203 for supplying a destaticizing solution are introduced into the funnel. A funnel 205 provided with a damper is arranged below the funnel 201 and a constant-volume receiver 206 for receiving the powdery sample dropped from the funnel 205 and a leveling bar 208 which slides on the upper surface of the receiver are arranged behind the funnel 205. The funnel 205 provided with a damper and the receiver 206 are those satisfying the requirements defined in JIS-K-6721. The receiver 206 is held and transported by a receiver-transporting robot 207. An electronic force balance 209 and a cleaner 210 for sucking the weighed powdery sample are arranged within the moving region of the receiver-transporting robot 207. The cleaner 210 is connected to an aspiration device.

Figure 8:
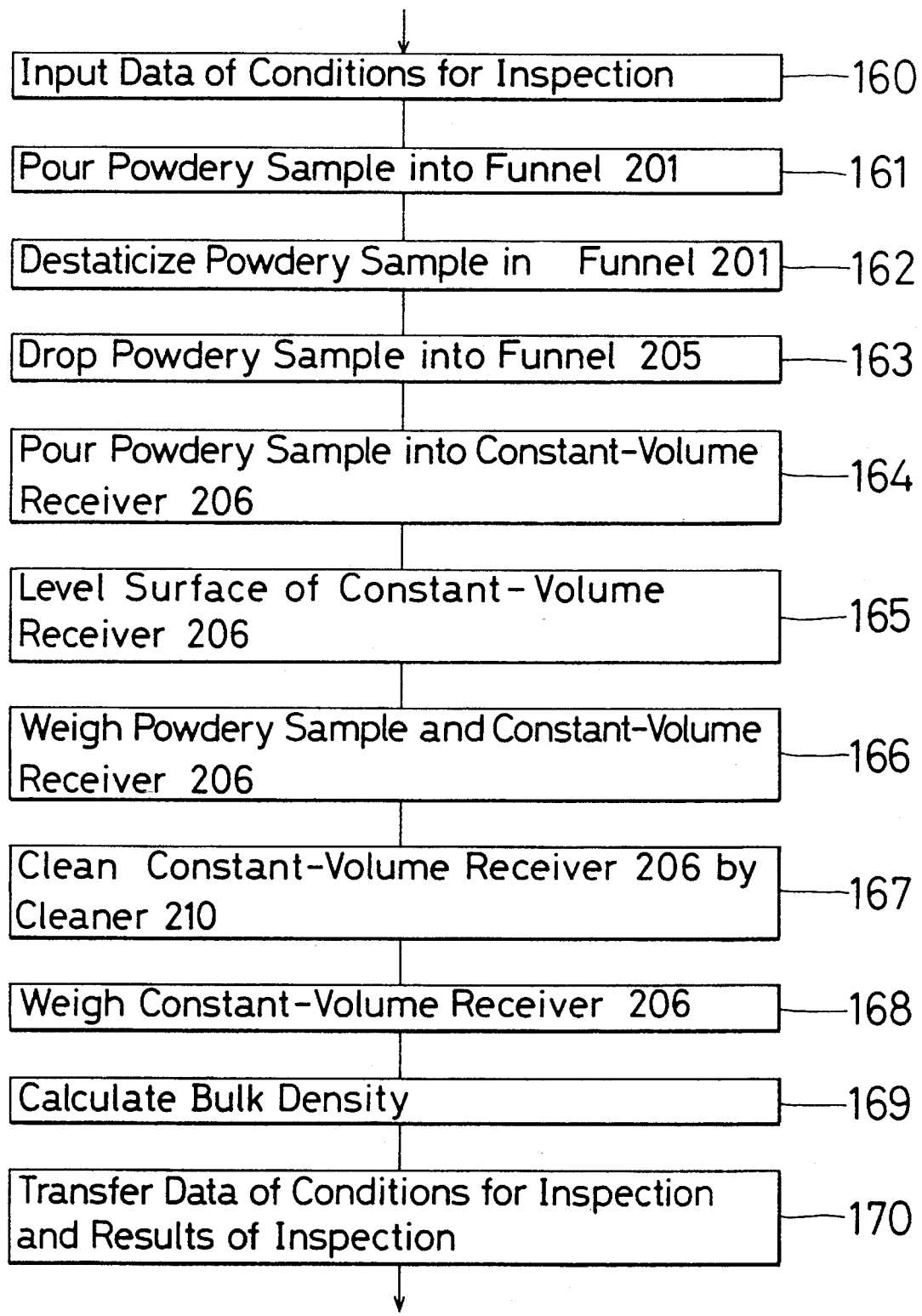
FIG. 8 is a flow chart showing the processing for determining bulk density which is equipped with a static eliminator.

The terminal computer 13 controls the determination of bulk density when the sample is destaticized according to the flow chart shown in FIG. 8. The subdivision of the sample in the sample bottle 9c conveyed by the conveyor 83 is pushed by an air cylinder (not shown) and put on a turn table 108. The data of conditions for inspection recorded in the bar code label 8c pasted on the sample bottle 9c for subdivision are read by the bar code reader 43 and, as shown in step 160 of the FIG. 8, inputted to the terminal computer 13 which directs the apparatus for determining particle size distribution to perform the detection of foreign substances of the sample and determination of the amounts thereof during rotating the turn table 108, then the action and control is shifted from the terminal computer 13 to the sequencer 53.

As shown in step 161, the powdery sample contained in the sample bottle 9c is poured into the funnel 201 by the robot 63 which operates through the action and control of the sequencer 53. As shown in step 162, according to the instruction of the sequencer 53, the destaticizing solution (a solution of a cationic surfactant) is fed into the funnel 201 through the tube 203, then the funnel 201 is rotated by the rotation of the motor 204 and the screw type stirring machine 202 is rotated by the rotation of the motor 212, and accordingly the powdery sample in the funnel 201 is destaticized as shown in step 162. On the other hand, the vacant sample bottle 9c is transferred by the robot 63 and discarded. As shown in step 163, the destaticized powdery sample in the funnel 201 is dropped into a funnel 205 provided with a damper by opening a bottom cover of the funnel 201. Then as shown in step 164, the damper of the funnel 205 is opened to drop the powdery sample in a constant-volume receiver 206. Thus the receiver 206 is heaped with the powdery sample and then, as shown in step 165, the surface of the sample is leveled by a leveling bar 208 to remove excess of the sample and to thus dispense a constant volume of the powdery sample. As shown step in 166, a receiver-transporting robot 207 operates and transports the constant-volume receiver 206 containing the dispensed powdery sample having a constant volume to an electronic force balance 209 for weighing the powdery sample. Then, as shown in step 167, the constant-volume receiver 206 is transferred, by the action of the receiver-transporting robot 207, to the cleaner 210 wherein the receiver is turned upside down and cleaned through aspiration by the cleaner 210. As shown in step 168, the vacant receiver 206 is returned to the electronic force balance 209 and again weighed.

As shown in step 169, these weights determined are inputted to the terminal computer 13 wherein the real weight of the sample is calculated on the basis of these inputted weights and the bulk density of the sample is then calculated from the real weight and the previously stored volume of the constant-volume receiver. As shown in step 170, the bulk density of the destaticized powdery sample thus calculated is inputted to the terminal computer 13 as a result of the inspection and transferred, through LAN 2, to the host computer 1 together with the data of conditions for inspection previously inputted to the computer 13.

[Determination of Bulk Density of Sample Which is not Destaticized]

Figure 9:
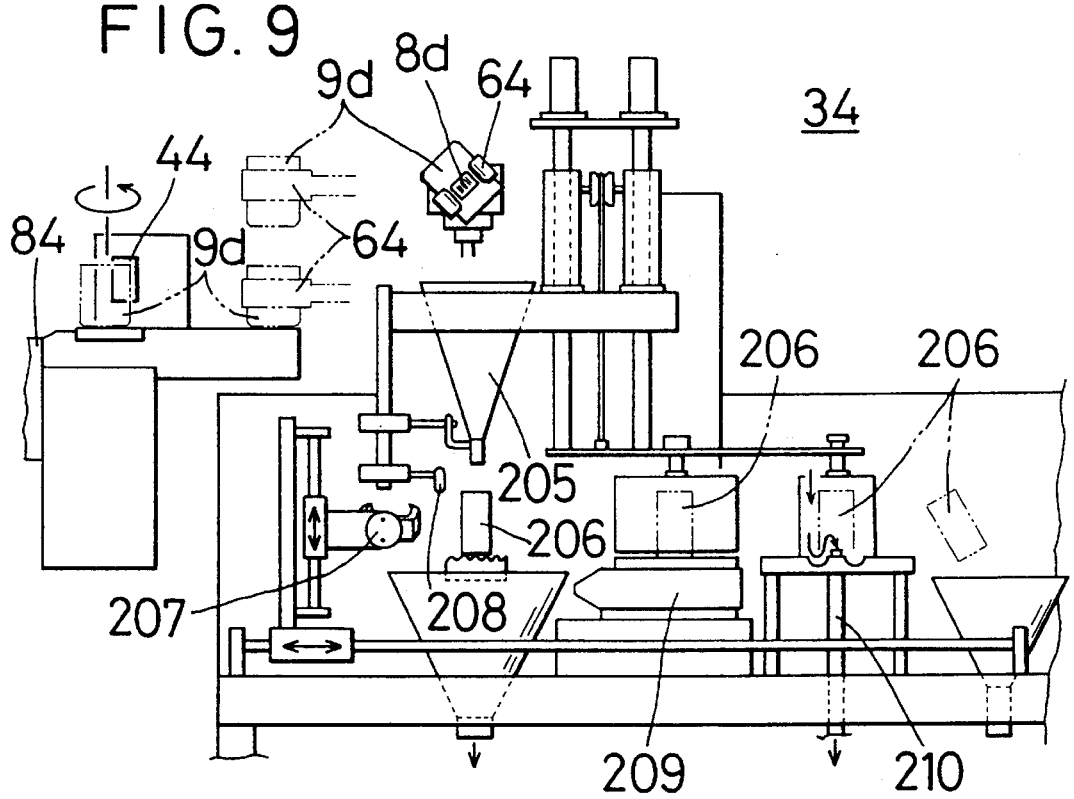
FIG. 9 is an elevational view of bulk density-determining device free of static eliminator.

A device 34 for determining bulk density without destaticization has a structure as shown in FIG. 9 as an elevational view. The device 34 for determining bulk density comprises a large number of parts common to those for the device 33 for determining bulk density provided with a static eliminator as shown in FIG. 7 and differs from the latter in that the former is not provided with the funnel 201, the motor 204, the screw type stirring machine 202 and the tube 203 for supplying the destaticizing solution. For this reason, the detailed explanation thereof will herein be omitted.

The terminal computer 14 controls the determination of the bulk density of a sample to be inspected when the sample is not destaticized. The subdivision of the sample in the sample bottle 9d conveyed by the conveyor 84 is transferred to the device 34 for determining bulk density through the action of the robot 64 which is driven and controlled by the sequencer 54. At this stage, the data of conditions for inspection recorded in the bar code label 8d pasted on the sample are read by the bar code reader 44 and inputted to the terminal computer 14 which directs the device for determining bulk density to perform the determination of the bulk density of the sample to be inspected which is not destaticized.

The function of the device 34 for determining bulk density is almost identical to that of the aforementioned device 33 for determining bulk density provided with a static eliminator. Only difference is that the powdery sample in the sample bottle 9d for subdivision is directly poured into the funnel 205 provided with a damper by the action of the robot 64. Other operations for determination are performed in the same manner used above and the resulting value of the bulk density of the powdery sample without destaticization is inputted to the terminal computer 14. The result of this inspection is transferred, through LAN 2, to the host computer 1 together with the data of conditions for inspection previously inputted to the computer 14.

[Precise Dispensing of Sample]

The subdivision of the sample in the sample bottle 9e for subdivision conveyed by the conveyor 80 is further precisely dispensed by the device 40 for precisely dispensing a powdery sample and the resulting precisely dispensed subdivisions are used for the determination of the degree of polymerization, the amounts of volatile components, the amounts of plasticizers absorbed and the amounts of remaining monomers.

Figure 10:
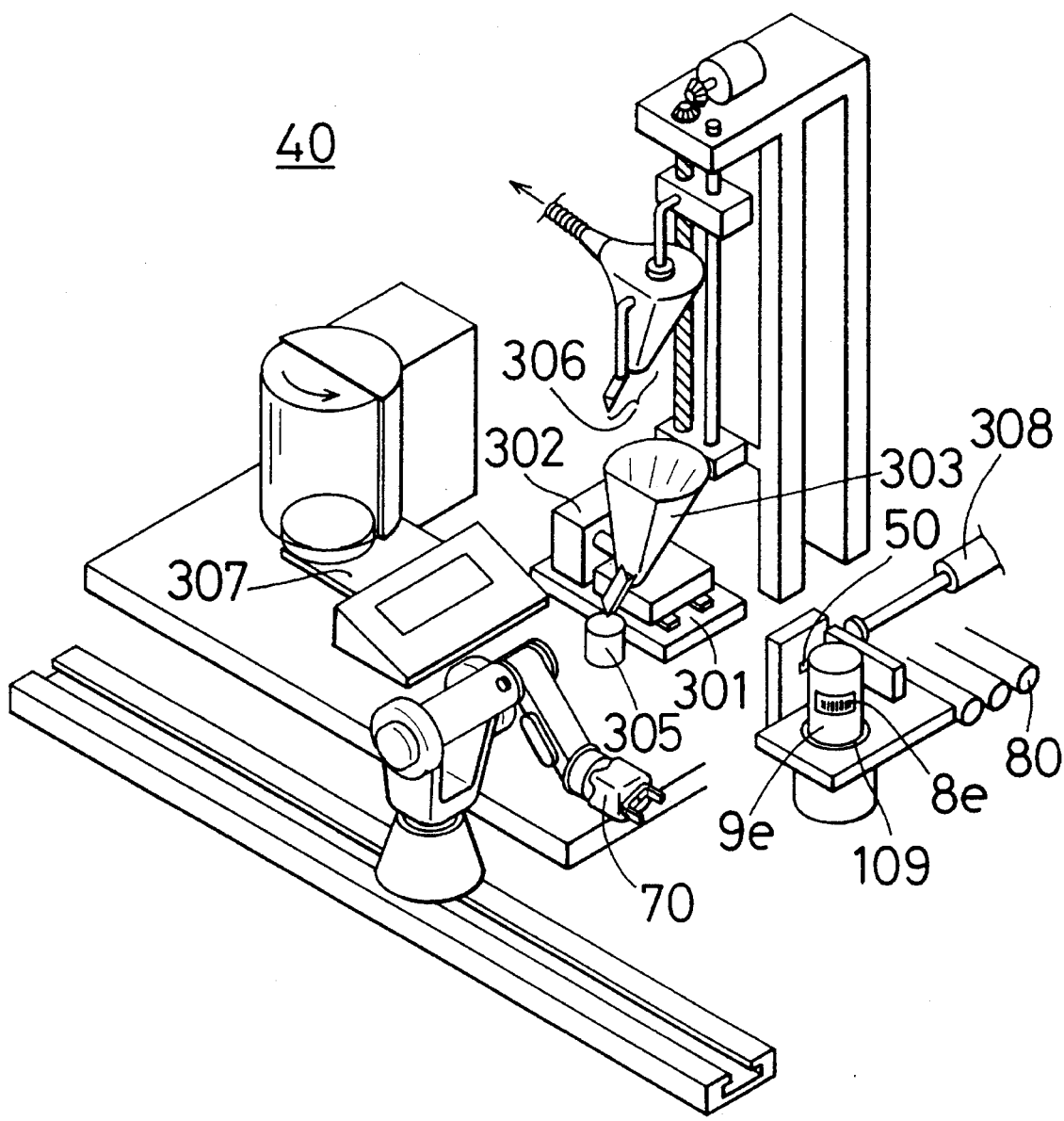
FIG. 10 is a perspective view showing a device for accurately dispensing a powdery sample.

As shown in FIG. 10 as a perspective view, the device 40 for precisely dispensing a sample comprises an electronic discharge-measuring device 301 and a hopper 303 which is mounted on the measuring device and connected to a control vibrator 302. An exhaust path which is connected to the lower opening of the hopper 303 has an inclination to an extent such that the powdery sample at rest does not flow, but flows by the vibration of the vibrator 302. An aspiration port 306 is disposed on the upper portion of the hopper 303 and it can move up and down so as to clean the hopper 303 and the exhaust path. In addition, an electronic force balance 307 is positioned in the proximity thereof.

The terminal computer 20 controls the precision dispensing of the powdery sample. The subdivision of the sample in the sample bottle 9e for subdivision conveyed by the conveyor 80 is pushed by an air cylinder 308 and put on a turn table 109. The data of conditions for inspection recorded in the bar code label 8e pasted on the sample bottle 9e for subdivision are read by the bar code reader 50 and inputted to the terminal computer 20 which directs, on the basis of the data of conditions for inspection, a desired apparatus for determining the degree of polymerization, the amounts of volatile components, the amounts of plasticizers absorbed or the amounts of remaining monomers during rotating the turn table 109. According to the direction, a desired amount of the sample is precisely dispensed in the corresponding sample container by the electronic exhaust measuring device 301. The precisely dispensed sample is further precisely weighed by an electronic force balance 307 depending on the item to be determined and the value thus precisely weighed is inputted to the terminal computer 20.

When the terminal computer 20 directs, for instance, the item of the determination of degree of polymerization, the direction is transferred to the terminal computer 15 for the determination of degree of polymerization. On the other hand, the sample contained 305 adapted for the determination of degree of polymerization is withdrawn from a table (not shown) by the action of the robot 70 which is driven and controlled by the sequencer 60 and placed under the discharge port of the electronic discharge-measuring device 301. The vibrator 302 is operated to discharge the powdery sample from the hopper 303 and the vibrator 302 is stopped at an instance when a desired amount of the sample required for the determination of degree of polymerization is weighed and discharged by the electronic discharge-measuring device 301. Thus a desired amount of the sample is introduced into the sample container 305. The container is placed on the conveyor 85 by the action of the robot 70 (see FIGS. 1B and 11).

In this respect, the amount of the powdery sample in the sample container must be precisely weighed in the determination of the amounts of plasticizers absorbed. In this case, the tare of the sample container and the weight of the sample container including the desired amount of the powdery sample are weighed by the electronic force balance 307 and the resulting real weight of the powdery sample is inputted to the terminal computer 17 for the determination of the amounts of plasticizers absorbed through the terminal computer 20.

Moreover, when the terminal computer 20 directs the apparatus to determine the amounts of volatile components, the amounts of plasticizers absorbed and the amounts of remaining monomers, desired amounts of the sample are dispensed in appropriate sample containers according to the procedures identical to those discussed above and these sample containers are placed on the conveyors 86 (see FIGS. 1B and 13), 87 (see FIGS. 1B and 14) and 88 (see FIGS. 1B and 15), respectively by the action of the robot 70.

[Determination of Degree of Polymerization]

The body 35A of the device 35 for determining degree of polymerization may be, for instance, a device for automatically determining degree of polymerization (VMR-052 PC, F01; available from Rigo Co., Ltd.). This device is in conformity with JIS K-6721 and, therefore, the details thereof are herein omitted. However, it is necessary to prepare a solution to be inspected having a desired concentration in order to use this device for automatically determining degree of polymerization.

Figure 11:
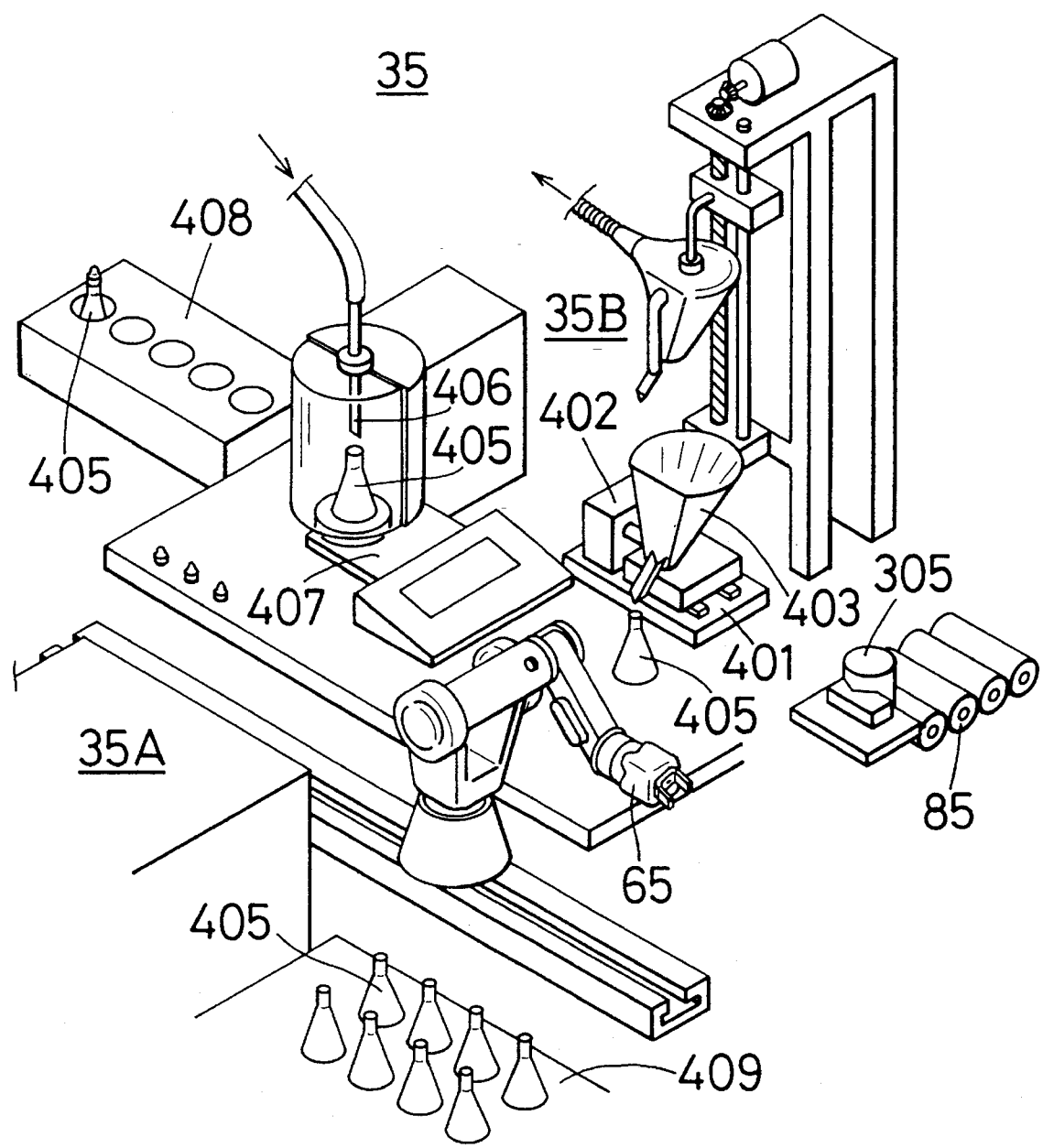
FIG. 11 is a perspective view showing a device for determining degree of polymerization.

The solution-preparing device 35B which is fitted to the device 35 for determining degree of polymerization comprises, as shown in FIG. 11 as a perspective view, an electronic discharge-measuring device 401 for detecting the amount of the powdery sample which is supplied from the sample container 305 to the hopper 403 and discharged from the hopper 403 by the action of the vibrator 402; a container 405 for dissolution which receives the powdery sample discharged from the hopper 403; an electronic force balance 407 for weighing the powdery sample contained in the container 405; a nozzle 406 for injecting a solvent (nitrobenzene) into the container 405 containing the powdery sample; and a device 408 for heating and stirring the powdery sample and the solvent in the container 405.

As described above in the item of Precise Dispensing of Sample, when the terminal computer 20 directs the item of the determination of degree of polymerization, the direction is transferred to the terminal computer 15 for the determination of degree of polymerization. The terminal computer 15 controls the determination of degree of polymerization. The device 35 for determining degree of polymerization operates as follows in accordance with a flow chart shown in FIG. 12 through the linked action and control of the terminal computer 15 and the sequencer 55. The powdery sample dispensed in the sample container 305 by the above-mentioned device 40 for precisely dispensing sample is transported to the solution-preparing device 35B by the conveyor 85, while it is heated and dried in the tunnel furnace in the course of the transportation.

Figure 12:
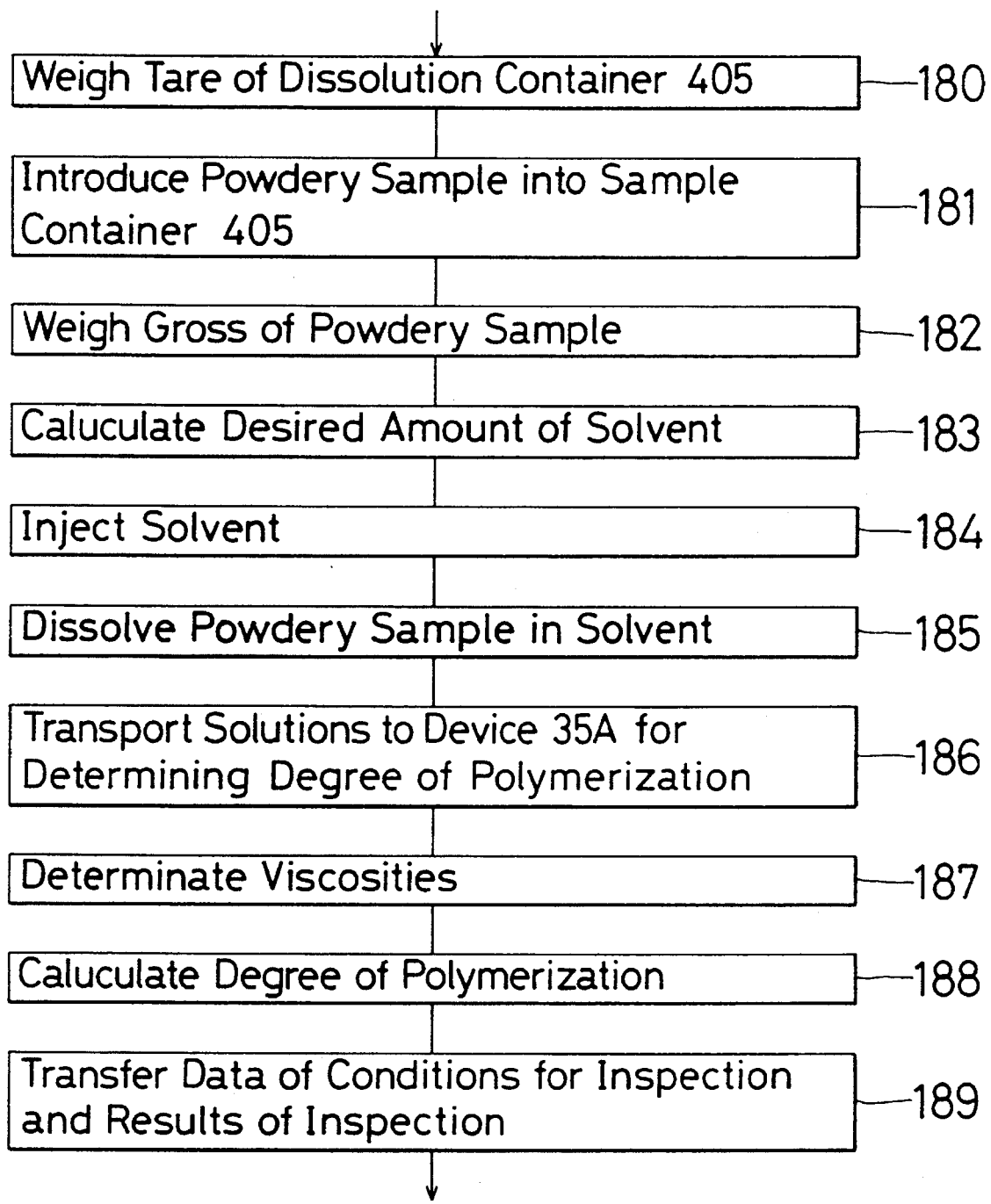
FIG. 12 is a flow chart showing the processing for determining degree of polymerization.

As shown in step 180 in FIG. 12, the dissolution container 405 placed on the table 409 is transferred, by the robot 65, to the electronic force balance 407 wherein the tare thereof is determined. The dissolution container 405 is placed under the discharge port of the electronic discharge-measuring device 401. As shown in step 181, the vibrator 402 is operated to discharge the powdery sample from the hopper 403 and the vibrator 402 is stopped at an instance when a desired amount of the sample required for the determination of degree of polymerization is weighed and discharged by the electronic discharge-measuring device 401. Thus a desired amount of the sample is introduced into the sample container 405. The container 405 is transferred to the electronic force balance 407 by the robot 65 to determine the weight thereof (step 182). As shown in step 183, the terminal computer 15 calculates a desired amount of a solvent based on the weight of the container and the foregoing tare. And the solvent is injected into the dissolution container 405 through the nozzle 406 in the amount thus determined as shown in step 184. The dissolution container 405 is transferred to the device 408 for heating and stirring by the action of the robot 65 to thus dissolve the powdery sample in the solvent and to thus prepare a solution to be inspected as shown in step 185.

After the preparation of a desired number of solutions to be inspected, as shown in step 186, they are transported to the body 35A of the device 35 for determining degree of polymerization and the door (the back side of FIG. 11) of the body 35A of the device 35 for determining degree of polymerization is opened and the dissolution containers 405 containing the solutions to be examined are placed, in the order of preparation, under a viscometer by the action of the robot 65. The door of the body 35A is closed and as shown in step 187, in accordance with the function of the device for determining degree of polymerization, the viscosities thereof are determined. As shown in step 188, the degree of polymerization is determined according to the known formula for converting an intrinsic viscosity into an average degree of polymerization by the terminal computer 15 from the viscosity data. As shown in step 189, the degree of polymerization is inputted to the terminal computer 15 as a result of inspection and then forwarded to the host computer 1 together with the data of conditions for inspection previously inputted from the terminal computer 20, through LAN 2.

[Determination of Contents of Volatile Components]

Figure 13B:
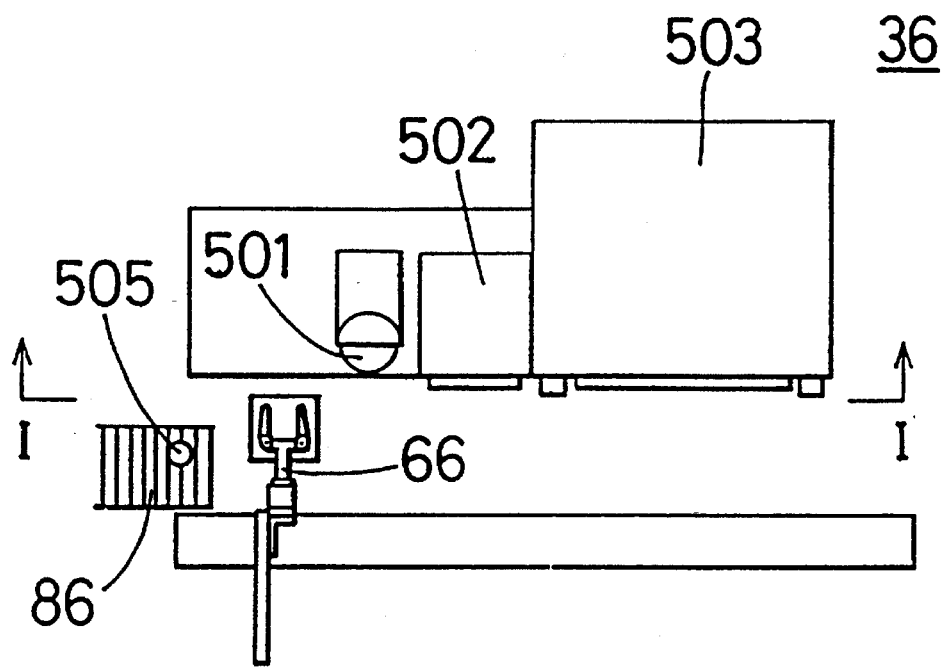
FIGS. 13A and 13B are an elevational view and a plain view showing a device for determining the amounts of volatile components, respectively.
Figure 13A:
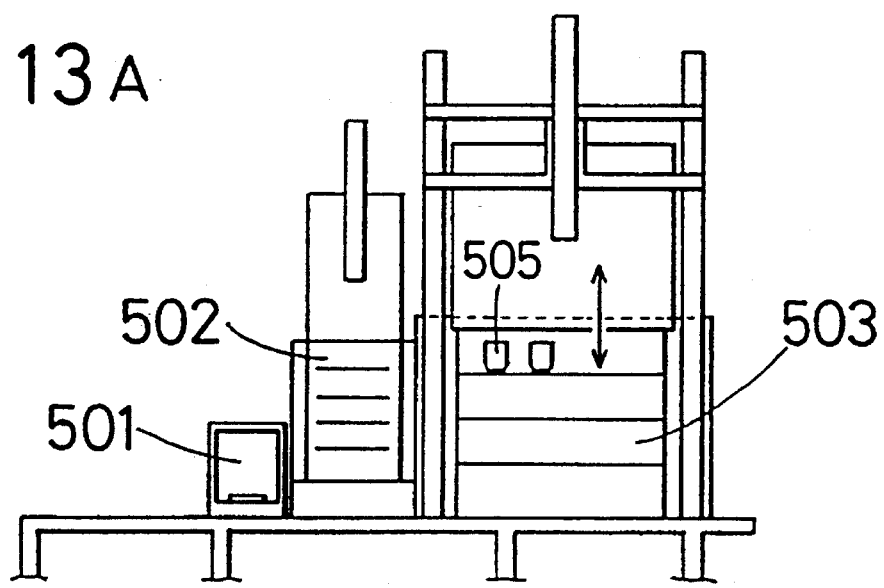

The device 36 for determining the contents of volatile components comprises, as shown in FIGS. 13B and 13A (a plain view and an elevational view taken along the line I—I of FIG. 13B), an electronic force balance 501, a cooling desiccator 502 and a drying furnace 503.

The terminal computer 16 controls the determination of the amounts of volatile components. The powdery sample dispensed in a drying container 505 by the device 40 for precisely dispensing sample is transported to the device 36 for determining the amounts of volatile components by the conveyor 86. The drying container 505 containing the powdery sample is transferred to the electronic force balance 501 by the robot 66 which is driven and controlled by the sequencer 56 and the weight of the container is determined therein. The measured weight thereof $W_1$ [$=w_1$ (the weight of the powdery sample prior to the drying)$+W_0$ (the weight of the drying container 505)]is inputted to the terminal computer 16. The weighed drying container 505 is transferred to the drying furnace 503 by the action of the robot 66. These operations are repeated to introduce a desired number of drying containers 505 in the drying furnace 503 and then the containers are allowed to stand in the drying furnace 503 maintained at a predetermined temperature for a desired period of time. After this treatment, the drying containers are transferred to the cooling desiccator 502 by the action of the robot 66 to cool them down to room temperature. They are transported to the electronic force balance 501 to again determine the weights thereof. The measured value $W_2$ [$=w_2$ (the weight of the powdery sample prior to the drying)$+W_0$ (the weight of the drying container 505)]is inputted to the terminal computer 16 wherein the content (%) of the volatile components is determined according to the relation: $(W_1-W_2) \times 100/W_1$. The data of the content of the volatile components are inputted to the terminal computer 16 and then forwarded to the host computer 1 together with the data of conditions for inspection previously inputted from the terminal computer 20, through LAN 2.

[Determination of the Amount of Plasticizers Absorbed]

Figure 14:
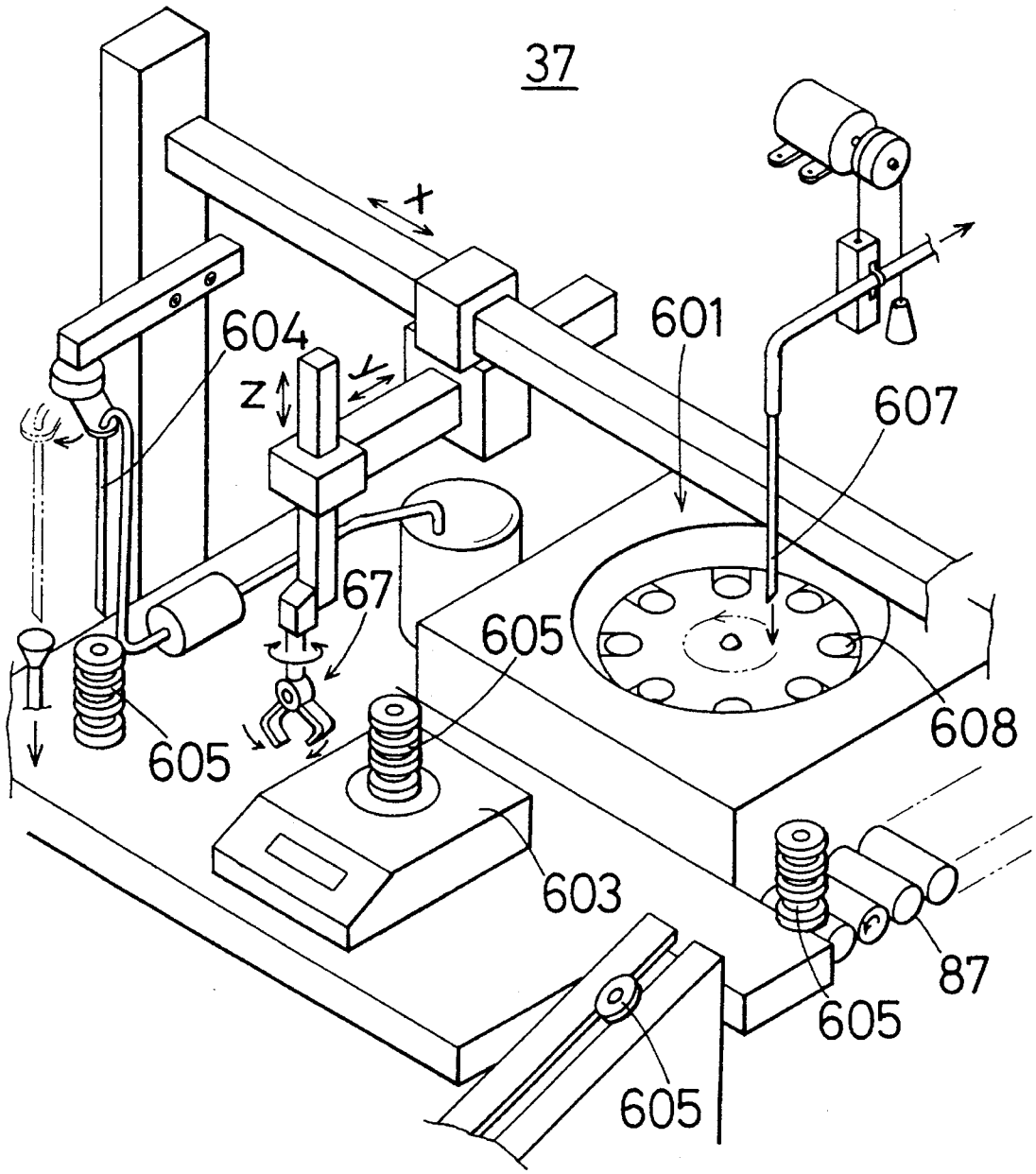
FIG. 14 is a perspective view showing a device for determining the amount of a plasticizer absorbed.

The device 37 for determining the amounts of plasticizers absorbed comprises, as shown in FIG. 14 as a perspective view, a plasticizer-supply tube 604 for injecting a plasticizer into an inspection container 605 containing a resin powder, a centrifugal separator 601, an electronic force balance 603 and a tube 607 for aspiration. A hole is formed on the bottom of the inspection container 605 and glass wool is packed therein so as to prevent any escape of the resin powder and to allow the permeation of the plasticizer. The centrifugal separator 601 is provided with a plurality of and an even number of envelopes having bottoms and rotating at a high speed.

The terminal computer 17 controls the determination of the amount of the plasticizer absorbed. The powdery sample is dispensed in the inspection container 605 by the device 40 for precisely dispensing sample, the inspection container 605 is introduced into a carrier container to precisely determine the weight thereof including the tare and the weight thus determined $W_0$ is transferred from the terminal computer 20 to the terminal computer 17. The inspection container 605 containing the powdery sample is transported to the device 37 for determining the amounts of plasticizers absorbed by the conveyor 87 together with the carrier container. The inspection container 605 is shifted from the conveyor 87 to the position below the plasticizer-supply tube 604 by the action of the robot 67 which is operated and controlled by the sequencer 57 and an excess of the plasticizer (such as dioctyl phthalate) is injected into the inspection container 605. The container 605 is withdrawn, by the robot 67, from the carrier container and inserted into the high speed envelope 608. These operations are repeated over even times and the containers are allowed to stand for a predetermined time to sufficiently permeate the plasticizer into the powdery sample. Thereafter, the centrifugal separator 601 is rotated at a predetermined number of revolutions and predetermined time period to remove the excess plasticizer which is not absorbed by the powdery sample, the excess plasticizer is accumulated on the bottom of the high speed envelope 608 through the bottom of the inspection container 605. After stopping the centrifugal separator, the inspection container 605 is removed from the high speed envelope 608, returned to the carrier container and transferred to the electronic force balance 603 in which the inspection container is weighed. The weight thus determined (i.e., the weight W of the powdery sample containing the plasticizer absorbed and including the tare) is inputted to the terminal computer 17. On the other hand, the aspiration tube 607 is inserted into the high speed rotating envelope 608 from which the inspection container 605 is removed to thus aspirate the plasticizer accumulated therein.

The foregoing procedures are repeated over the times equal to the number of samples. The weight $W_0$ of the powdery sample prior to absorb the plasticizer and the weight W of the powdery sample after absorbing the plasticizer are inputted to the terminal computer 17 wherein the amount (rate) of the plasticizer absorbed is calculated according to the relation: $(W-W_0)/W_0$. The data of the amount of the plasticizer absorbed is inputted to the terminal computer 17 and then forwarded to the host computer 1 together with the data of conditions for inspection previously inputted from the terminal computer 20, through LAN 2.

[Determination of the Amount of Remaining Monomer]

Figure 15:
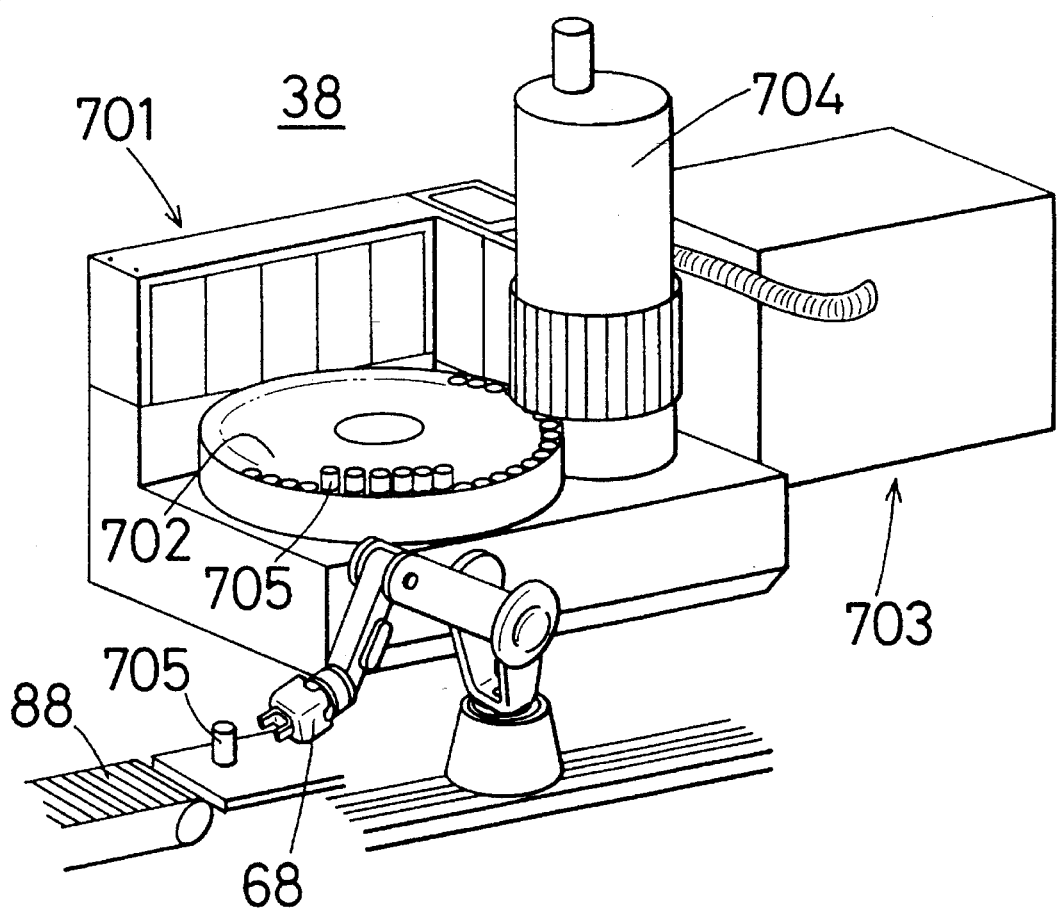
FIG. 15 is a perspective view showing a device for determining the amounts of remaining monomers.

To determine the amount of a remaining monomer, a cartridge container 705 which contains the powdery sample and is airtightly sealed is heated to a predetermined temperature to thus force out the remaining monomer included in the powdery sample into the gas phase of the cartridge container 705. The gas in the gas phase is sampled by introducing a needle into the gas phase through the cartridge wall and subjected to quantitative analysis through the gas chromatography. The sampler for sampling the gas in the gas phase used herein may be, for instance, Head Space H Step-40 available from Perkin Elmer Company. In addition, the gas chromatograph usable herein may, for instance, be Gas Chromatograph Model 8700 likewise available from Perkin Elmer Company. Such a device 38 for determining the amount of the remaining monomer comprises, as shown in FIG. 15 as a perspective view, a gas chromatographic analyzer 703 communicated to a sampler 701. The sampler 701 comprises a rotary type magazine 702 and a sampling unit 704.

The terminal computer 18 controls the determination of the amount of the remaining monomer. The cartridge container 705 which contains the powdery sample dispensed by the device 40 for precisely dispensing sample and precisely weighed is airtightly sealed by a cap made of a material capable of being pricked with a needle through the use of an automatic capping device (not shown) and transferred to the device 38 for determining the amount of the remaining monomer by the action of the conveyor 88. The cartridge containers 705 are in order introduced into the magazine 702 by the action of the robot 68 which is driven and controlled by the sequencer 58 while the magazine 702 rotates, thus the cartridge containers 705 are heated at a desired temperature for a predetermined period of time in the sampling unit 704 and then the cartridge containers 705 are, in order, pricked with a needle to perform sampling. The gas in the gas phase of the cartridge container 705 sampled through pricking with the needle in the sampling unit 704 is transferred to the chromatographic analyzer 703 in which the gas is quantitatively analyzed. Thus, the amount of the remaining monomer separated from the powdery sample is determined. The terminal computer 18 calculates a ratio of the amount of the remaining monomer to the precise weight of the powdery sample in the cartridge container 705 previously inputted to the terminal computer 18 from the terminal computer 20 for the device 40 for precisely dispensing sample and the resulting ratio is stored therein as the measured value for the amount of the remaining monomer. The measured value for the remaining monomer is forwarded to host computer 1 through LAN 2 together with the data of conditions for inspection previously inputted from the terminal computer 20.

The results of inspection transferred to the host computer 1 in each determination step are stored in the memory 23 (see FIG. 3) in correspondence to the data of conditions for inspection simultaneously transferred to the host computer 1. The results of inspection are compared with the product data and the quality standards through the inspection number of the data of conditions for inspection.

Figure 3:
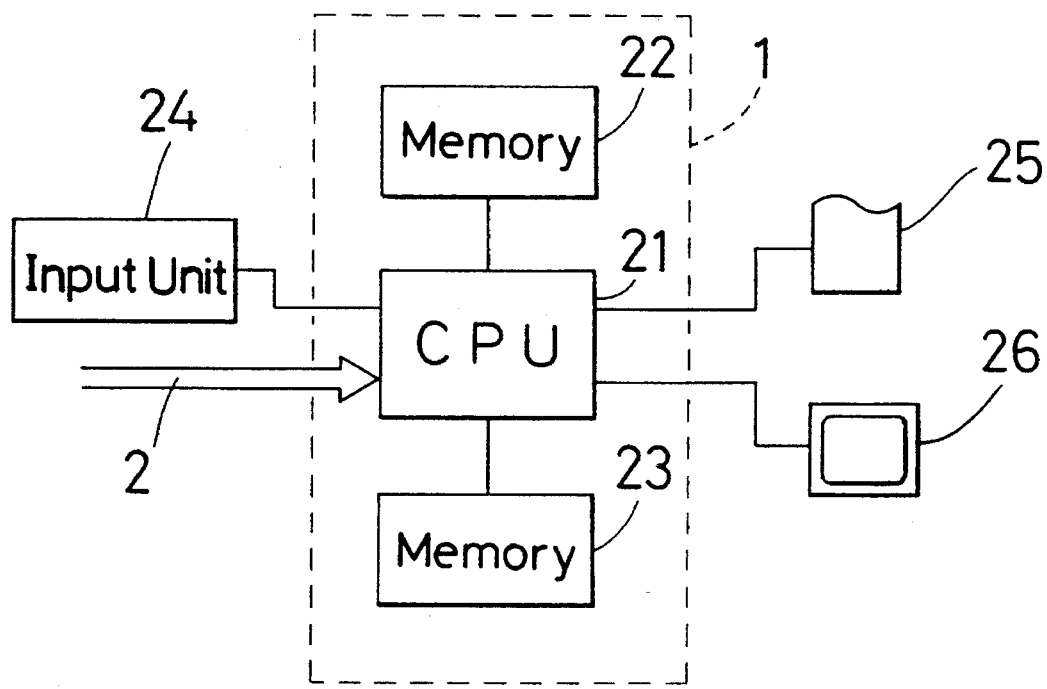
FIG. 3 is a block diagram illustrating the main control unit used in the apparatus for automatically inspecting powdery products according to the present invention.
Figure 16:
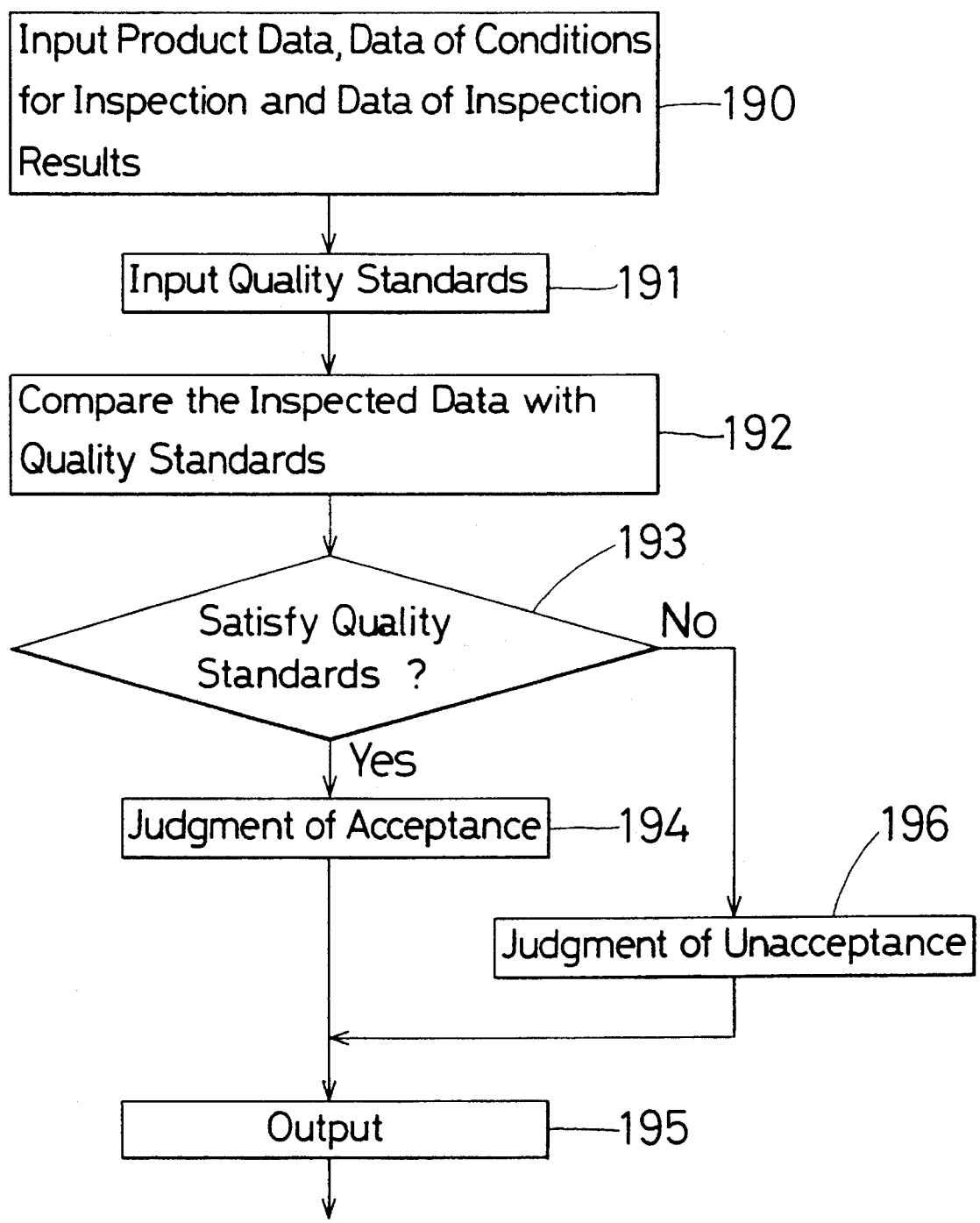
FIG. 16 is a flow chart showing the processing for judgment of product quality, which is performed in the main control unit of the apparatus according to the present invention.

The judgment of the quality of the sample which is performed by the circuit as shown in FIG. 3 will hereinafter be explained with reference to the flow chart shown in FIG. 16.

If the results of inspection are inputted to CPU 21 of the host computer 1 along with the product data and the data of conditions for inspection (step 190), CPU 21 accepts the quality standards, outputted from the memory 22, corresponding to the product data and the data of conditions for inspection (step 191). A series of the inspection results are compared with the quality standards for each item to be inspected according to the program for judging the quality of the sample (step 192) and thus the quality of the sample is judged (step 193). When the inspected results satisfy the quality standards, the sample is judged to be acceptable (step 194) and the result of judgment is outputted (step 195) and stored in the memory 23. While if the inspected results do not satisfy the quality standards, the sample is judged to be unacceptable (step 196) and the result of judgment is likewise outputted (step 195) and stored in the memory 23. Alternatively, the results of judgment are printed out by the printer 25 or displayed on the display device 26. The comparison of the inspected results with the quality standards and the judgment of the quality may be performed each time the results of each inspection are inputted to the host computer 1 after the completion of each inspection or may be collectively be performed after the results of a plurality of inspections are inputted to the host computer 1.

In the foregoing embodiments, there have been explained a case where each subdivision of the sample to be inspected is correctly transferred to the corresponding device for determination. However, if a subdivision of the sample is, for instance, transferred to a wrong automatic inspection device, the inspection of the subdivision of the sample is judged to be interrupted at the time when the data of conditions for inspection are read since the inspection item among the data of conditions for inspection attached to the subdivision of the sample does not direct the device to perform the corresponding determination and, accordingly, the automatic inspection devices 31 to 34 are interrupted. This is also true in a case where a subdivision of the sample which does not require precise dispensing is transferred to the device 40 for precisely dispensing the sample. Either the terminal computers 11 to 14 and 20 or the host computer 1 may be designed to perform such judgment.

What is claimed is:

1. An apparatus for automatically inspecting a plastic powdery sample comprising means for reading sample data attached to the sample;

means for subdividing the sample into subdivisions;

a plurality of automatic inspection means, each of which processes, in parallel, each subdivision of the sample;

a computer for calculating condition data for each inspection from the sample data read by the reading means;

means for recording the condition data of each subdivision of the sample;

a plurality of means for reading the condition data; and a plurality of computers each of which controls the operation of each inspection means from the condition data read by the reading means, wherein the plurality of automatic inspection means comprises a means for determining bulk density when the sample is destaticized, a means for determining bulk density when the sample is not destaticized and at least one of a means for determining an amount of a volatile component and a means for determining an amount of a plasticizer absorbed.

2. The apparatus of claim 1, wherein the plurality of automatic inspection means comprises a means for determining an amount of a remaining monomer, a means for determining degree of polymerization, a means for determining an amount of a volatile component, a means for determining an amount of a plasticizer absorbed, a means for determining particle size distribution, a means for determining foreign substances, a means for determining bulk density when the sample is destaticized, and a means for determining bulk density when the sample is not destaticized.

3. The apparatus of claim 1, wherein the means for determining bulk density comprises a funnel provided with a damper for detaining the powdery sample; a constant-volume receiver to receive the powdery sample dropped from the funnel; a leveling bar for sliding on the upper surface of the receiver; and an electronic force balance for weighing the powdery sample in the constant volume receiver.

4. The apparatus of claim 1, wherein the means for determining bulk density comprises a static eliminator for destaticizing electric charges of the powdery sample by mixing a destaticizing solution into the powdery sample; a funnel provided with a damper for detaining the powdery sample; a constant-volume receiver to receive the powdery sample dropped from the funnel; a leveling bar for sliding on the upper surface of the receiver; and an electronic force balance for weighing the powdery sample in the receiver.

5. The apparatus of claim 1, wherein the sample data and condition data are bar code data; the means for reading the sample data and the condition data are bar code readers; and the means for recording the condition data is a bar code printer.

6. The apparatus of claim 1, wherein the computer for calculating the condition data and the plurality of computers are connected to a host computer to which data read by each of the automatic inspection means, the sample data, and the condition data are transmitted.

7. The apparatus of claim 6, wherein the host computer has a function for comparing the inspected data transmitted thereto with quality standard data calculated from the sample data and the condition data transmitted thereto to judge the quality of the sample.

8. The apparatus of claim 1, wherein the powdery plastic sample is vinyl chloride resin powder.

9. The apparatus of claim 1, wherein the means for determining bulk density when the sample is not destaticized comprises a funnel provided with a damper for detaining the powdery sample; a constant-volume receiver to receive the powdery sample dropped from the funnel; a leveling bar for sliding on the upper surface of the receiver; and an electronic force balance for weighing the powdery sample in the constant-volume receiver.

10. The apparatus of claim 1, wherein the means for determining bulk density when the sample is destaticized comprises a static eliminator for destaticizing electric charges of the powdery sample by mixing a destaticizing solution into the powdery sample; a funnel provided with a damper for detaining the powdery sample; a constant-volume receiver to receive the powdery sample dropped from the funnel a leveling bar for sliding on the upper surface of the receiver; and an electronic force balance for weighing the powdery sample in the receiver.

* * * * *